United States Patent
Shiratani

(10) Patent No.: US 12,417,531 B2
(45) Date of Patent: Sep. 16, 2025

(54) IMAGE PROCESSING SYSTEM, TRAINING METHOD FOR TRAINING DEVICE, AND STORAGE MEDIUM

(71) Applicant: OLYMPUS CORPORATION, Tokyo (JP)

(72) Inventor: Fumiyuki Shiratani, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 662 days.

(21) Appl. No.: 17/857,385

(22) Filed: Jul. 5, 2022

(65) Prior Publication Data
US 2022/0335610 A1    Oct. 20, 2022

Related U.S. Application Data

(63) Continuation of application No. PCT/JP2020/000377, filed on Jan. 9, 2020.

(51) Int. Cl.
*G06T 7/00* (2017.01)

(52) U.S. Cl.
CPC .. *G06T 7/0012* (2013.01); *G06T 2207/10068* (2013.01); *G06T 2207/20081* (2013.01);
(Continued)

(58) Field of Classification Search
CPC ......... G06T 7/0012; G06T 2207/10068; G06T 2207/20081; G06T 2207/20084; G06T 2207/30032
See application file for complete search history.

(56) References Cited

U.S. PATENT DOCUMENTS 9,336,591 B2 * 5/2016 Mallya ................... A61N 5/103
10,861,151 B2   12/2020 Liang et al.
(Continued)

FOREIGN PATENT DOCUMENTS

CN    109523532 A    3/2019
JP    2002-083301 A   3/2002
(Continued)

OTHER PUBLICATIONS

Translation of WO 2020003991 A1 from EPO (Year: 2020).*
(Continued)

*Primary Examiner* — Lewis G West
(74) *Attorney, Agent, or Firm* — Scully, Scott, Murphy & Presser, P.C.

(57) ABSTRACT

An image processing system includes a processor configured to acquire, as a processing target image, an in-vivo image, operate in accordance with a trained model, and output a recognition result representing a result of recognition of a region of interest in the processing target image. The trained model is trained by having undergone pre-training using a first image group including images captured in a first observation method, and having undergone, after the pre-training, fine-tuning that uses a second image group including images captured in a second observation method, as well as that uses ground truth regarding the region of interest included in the second image group. The first observation method is an observation method using normal light as illumination light, and the second observation method is an observation method using special light as the illumination light or an observation method in which a pigment has been dispersed onto the subject.

15 Claims, 13 Drawing Sheets

(52) U.S. Cl.
CPC .............. *G06T 2207/20084* (2013.01); *G06T 2207/30032* (2013.01)

(56) References Cited

U.S. PATENT DOCUMENTS

| | | | |
|---|---|---|---|
| 10,986,987 | B2 | 4/2021 | Aoyama et al. |
| 11,109,748 | B2 | 9/2021 | Okada |
| 2006/0184039 | A1* | 8/2006 | Avni ............... H04N 23/74 600/476 |
| 2007/0133071 | A1 | 6/2007 | Noyes et al. |
| 2012/0296218 | A1 | 11/2012 | Ishihara |
| 2013/0258080 | A1 | 10/2013 | Kuriyama |
| 2014/0049626 | A1 | 2/2014 | Ishihara |
| 2014/0184769 | A1 | 7/2014 | Ishihara et al. |
| 2015/0363670 | A1 | 12/2015 | Sugishita et al. |
| 2017/0296034 | A1 | 10/2017 | Sasaki |
| 2018/0225820 | A1 | 8/2018 | Liang et al. |
| 2019/0034800 | A1 | 1/2019 | Shiratani |
| 2019/0311476 | A1* | 10/2019 | Hayami ............... A61B 5/7264 |
| 2020/0288076 | A1* | 9/2020 | Kozuka ............... H04N 25/77 |
| 2020/0320702 | A1 | 10/2020 | Kamon |
| 2021/0027056 | A1* | 1/2021 | Koch ............... G06F 18/214 |
| 2021/0153730 | A1 | 5/2021 | Karino |
| 2021/0166385 | A1 | 6/2021 | Shang et al. |
| 2022/0351483 | A1 | 11/2022 | Shiratani |
| 2023/0072596 | A1 | 3/2023 | Kamimura |
| 2024/0099577 | A1* | 3/2024 | Park ............... A61B 3/12 |

FOREIGN PATENT DOCUMENTS

| | | |
|---|---|---|
| JP | 2004-351100 A | 12/2004 |
| JP | 2007-140823 A | 6/2007 |
| JP | 2009-518982 A | 5/2009 |
| JP | 2011-161046 A | 8/2011 |
| JP | 2012-115554 A | 6/2012 |
| JP | 2013-056001 A | 3/2013 |
| JP | 2016-015116 A | 1/2016 |
| WO | 2012/147820 A1 | 11/2012 |
| WO | 2016/110984 A1 | 7/2016 |
| WO | 2017/175282 A1 | 10/2017 |
| WO | 2018/105063 A1 | 6/2018 |
| WO | 2019/138773 A1 | 7/2019 |
| WO | 2020/003991 A1 | 1/2020 |

OTHER PUBLICATIONS

International Search Report dated Mar. 24, 2020 received in PCT/JP2020/000375.
International Search Report dated Feb. 25, 2020 received in PCT/JP2020/000377.
Nima Tajbakhsh et al., "Convolutional Neural Networks for Medical Image Analysis: Full Training or Fine Tuning?", IEEE Transactions on Medical Imaging. May 2016.No. 5 , p. 1229-1312.
Liu, Xiaoqi, et al., Fine-tuning Pre-trained Convolutional Neural Networks for Gastric Precancerous Disease Classification on Magnification Narrow-band Imaging Images, Nerucomputing, 2019, ISSN:0925-2312, DOI:10.1016-j.neucom.2018.10.100.
International Search Report dated Mar. 17, 2020 received in PCT/JP2020/000376.
US Office Action issued Sep. 23, 2024 in U.S. Appl. No. 17/857,363.
Mohan et al. "Example-Based Object Detection in Images by Components", IEEE transactions on Pattern Analysis and Machine Intelligence, vol. 23, No. 4, Apr. 2001, pp. 349-361.

* cited by examiner

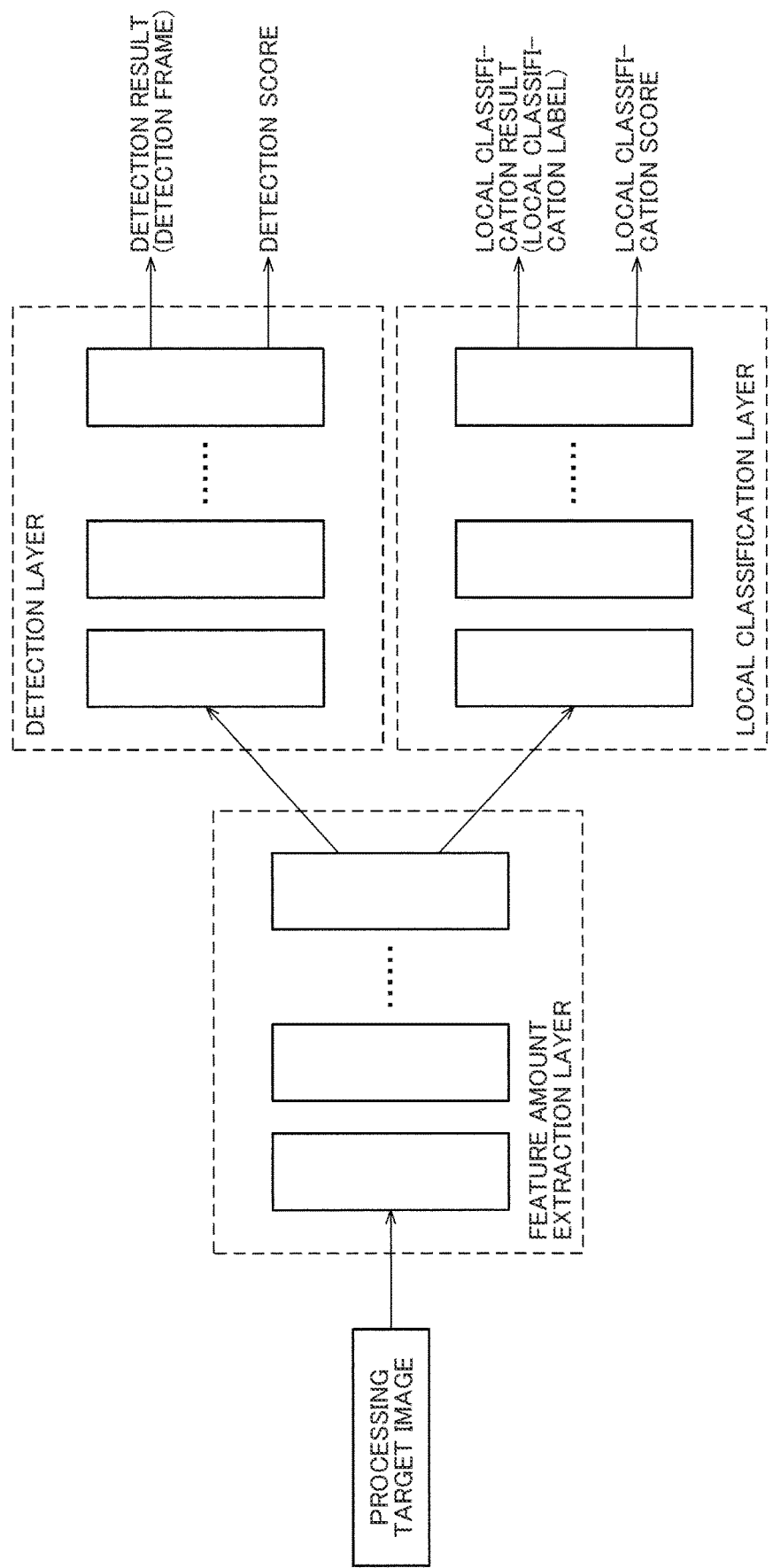

IMAGE PROCESSING SYSTEM, TRAINING METHOD FOR TRAINING DEVICE, AND STORAGE MEDIUM

CROSS REFERENCE TO RELATED APPLICATION

This application is a continuation of International Patent Application No. PCT/JP2020/000377, having an international filing date of Jan. 9, 2020, which designated the United States, the entirety of which is incorporated herein by reference.

BACKGROUND

A method of performing an image process targeting an in-vivo image to support a doctor's diagnosis has been widely known. Specifically, an attempt has been made to apply image recognition by deep learning to detection of a lesion and differentiation of a degree of malignancy. However, with training by deep learning, recognition with high accuracy cannot be obtained under a situation without an abundance of training data (learning data).

For example, Nima Tajbakhsh et al., "Convolutional Neural Networks for Medical Image Analysis: Full Training or Fine Tuning?", IEEE TRANSACTIONS ON MEDICAL IMAGING. 2016 May. NO. 5, p. 1229-1312, discloses that a training device having undergone pre-training that uses ImageNet that is greater in number and then having undergone fine-tuning that uses endoscope images exhibits higher accuracy of detection of a lesion than a training device having undergone full-training that uses only endoscope images that are lesser in number. The ImageNet is a dataset comprising general object images.

International Patent Application No. 2017/175282 discloses a method of using endoscope images at a higher frame rate for pre-training on capsule endoscope images at a lower frame rate and thereby supplementing insufficiency of training images each showing a landmark such as the pylorus of the stomach and the ileocecal valve of the large intestine.

SUMMARY

In accordance with one of some aspect, there is provided a n image processing system comprising a processor including hardware, the processor being configured to acquire, as a processing target image, an in-vivo image captured by an endoscope imaging device, operate in accordance with a trained model, and output a recognition result representing a result of recognition of a region of interest in the processing target image, the trained model being trained by having undergone pre-training that uses a first image group including images captured in a first observation method, and then having undergone, after the pre-training, fine-tuning that uses a second image group including images captured in a second observation method, as well as that uses ground truth regarding the region of interest included in the second image group, the first observation method being an observation method that uses normal light as illumination light, the second observation method being an observation method that uses special light as the illumination light or an observation method in which a pigment has been sprayed onto a subject, the second image group including at least one image captured with the region of interest, and the second image group being lesser in number of images than the first image group.

In accordance with one of some aspect, there is provided a training device comprising a processor including hardware, the processor being configured to acquire, a first image group including images captured in a first observation method and a second image group including images captured in a second observation method, generate a trained model that outputs, when a processing target image is input to the trained model, a recognition result representing a result of recognition of a region of interest in the processing target image by having undergone pre-training that uses the first image group, and then having undergone, after the pre-training, fine-tuning that uses the second image group, as well as that uses ground truth regarding the region of interest included in the second image group, the first observation method being an observation method that uses normal light as illumination light, the second observation method being an observation method that uses special light as the illumination light or an observation method in which a pigment has been sprayed onto a subject, the second image group including at least one image captured with the region of interest, and the second image group being lesser in number of images than the first image group.

In accordance with one of some aspect, there is provided a training method comprising: acquiring a first image group including images captured in a first observation method and a second image group including images captured in a second observation method; generating a trained model that outputs, when a processing target image is input to the trained model, a recognition result representing a result of recognition of a region of interest in the processing target image by having undergone pre-training that uses the first image group, and then having undergone, after the pre-training, fine-tuning that uses the second image group, as well as that uses ground truth regarding the region of interest included in the second image group, the first observation method being an observation method that uses normal light as illumination light, the second observation method being an observation method that uses special light as the illumination light or an observation method in which a pigment has been sprayed onto a subject, the second image group including at least one image captured with the region of interest, and the second image group being lesser in number of images than the first image group.

In accordance with one of some aspect, there is provided a computer readable non-transitory storage medium that stores a program that causes a computer to execute steps of: acquiring, as a processing target image, an in-vivo image captured by an endoscope imaging device; operating in accordance with a trained model, and outputting a recognition result representing a result of recognition of a region of interest in the processing target image, the trained model being trained by having undergone pre-training that uses a first image group including images captured in a first observation method, and then having undergone, after the pre-training, fine-tuning that uses a second image group including images captured in a second observation method, as well as that uses ground truth regarding the region of interest included in the second image group, the first observation method being an observation method that uses normal light as illumination light, the second observation method being an observation method that uses special light as the illumination light or an observation method in which a pigment has been sprayed onto a subject, the second image group including at least one image captured with the region of interest, and the second image group being lesser in number of images than the first image group.

BRIEF DESCRIPTION OF THE DRAWINGS

FIG. 6 illustrates a configuration example of a convolutional neural network (CNN) in accordance with the present embodiment.

DESCRIPTION OF EXEMPLARY EMBODIMENTS

Figure 1:
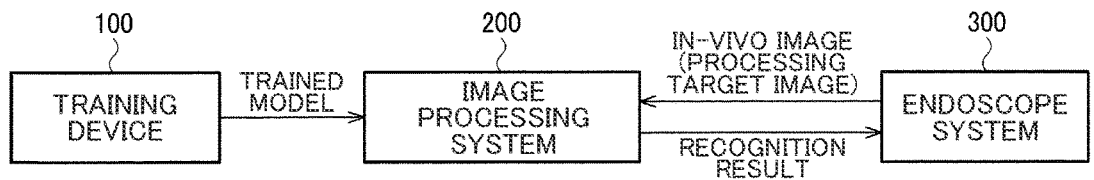
FIG. 1 illustrates a schematic configuration example of a system including an image processing system.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

Exemplary embodiments are described below. Note that the following exemplary embodiments do not in any way limit the scope of the content defined by the claims laid out herein. Note also that all of the elements described in the present embodiment should not necessarily be taken as essential elements 1. Overview When a doctor makes a diagnosis using an endoscope system, various kinds of observation methods are used. The observation mentioned herein is, specifically, to see a state of a subject using a captured image. The captured image is, specifically, an in-vivo image. The observation method changes depending on a type of illumination light of an endoscope apparatus and the state of the subject. As the observation method, normal light observation, special light observation, pigment spray observation, and the like can be assumed. In the normal light observation method, normal light is emitted as illumination light and image-capturing is thereby performed. In the special light observation method, special light is emitted as illumination light and image-capturing is thereby performed. In the pigment spray observation method, image-capturing is performed in a state where a dye is sprayed onto a subject. In the following description, an image captured in normal light observation is referred to as a normal light image, an image captured in special light observation is referred to as a special light image, and an image captured in pigment spray observation is referred to as a pigment-sprayed image.

The normal light is light having an intensity in a wide wavelength band out of wavelength bands corresponding to visible light, and is white light in a more limited sense. The special light is light having spectral characteristics different from those of the normal light, and is, for example, narrow band light having a wavelength band that is narrower than that of the normal light. Conceivable examples of an observation method that uses the special light include a narrow band imaging (NBI) method that uses narrow band light corresponding to a wavelength of 390 to 445 nm and narrow band light corresponding to a wavelength of 530 to 550 nm. The special light may include light having a wavelength band of light other than visible light such as infrared light. As the special light used for the special light observation, light having various kinds of wavelength bands has been known and a wide range of light is applicable to the present embodiment. A die used in the pigment spray observation is, for example, indigocarmine. Dispersing the indigocarmine can increase visibility of a polyp. Various kinds of die and various combinations of regions of interest to be targeted have been known, and a wide range of them is applicable to the pigment spray observation in accordance with the present embodiment.

For example, as a diagnosis step performed by a doctor, a step of searching for a lesion using the normal light observation and a step of differentiating a degree of malignancy of a detected lesion using the special light observation or the pigment spray observation can be assumed. The special light image and the pigment-sprayed image each provide higher visibility of a lesion than that in the normal light image, and thus enable differentiation of a degree of malignancy with high accuracy.

As described above, an attempt has been made to apply image recognition by deep learning to detection of a lesion and differentiation of a degree of malignancy for the purpose of supporting the doctor's diagnosis. With training by deep learning, high recognition accuracy cannot be obtained under a situation without an abundance of training data. Since the special light image and the pigment-sprayed image cannot always be obtained in abundance like the normal light image, the situation corresponds to a situation where the training data is not abundant.

To address insufficiency of the training data, a method of performing pre-training and fine-tuning has been known, as discussed in International Patent Application No. 2017/175282 and Nima Tajbakhsh et al., "Convolutional Neural Networks for Medical Image Analysis: Full Training or Fine Tuning?", IEEE TRANSACTIONS ON MEDICAL IMAG- ING. 2016 May. NO. 5, p. 1229-1312. However, in Nima Tajbakhsh et al., "Convolutional Neural Networks for Medical Image Analysis: Full Training or Fine Tuning?", IEEE TRANSACTIONS ON MEDICAL IMAGING. 2016 May. NO. 5, p. 1229-1312, an image different from an endoscope image is used for pre-training. A difference in category between pre-training and fine-tuning is large, and there is a possibility that an effect of increasing recognition accuracy targeting the endoscope image is insufficient. The method of International Patent Application No. 2017/175282 is a method in consideration of insufficiency of images captured with a specific subject due to a low frame rate of a capsule endoscope. In International Patent Application No. 2017/175282, consideration is not given to a difference of observation methods between the special light image and the normal light image and a difference of observation methods between the pigment-sprayed image and the normal light image. Deep learning exhibits decreased recognition performance with respect to a test image captured under a condition that is different from that of an image group used for the training. The test image mentioned herein represents an image serving as a target of an inference process using a result of the training. That is, as conventional methods including the method of International Patent Application No. 2017/175282 and the method of Nima Tajbakhsh et al., "Convolutional Neural Networks for Medical Image Analysis: Full Training or Fine Tuning?", IEEE TRANSACTIONS ON MEDICAL IMAGING. 2016 May. NO. 5, p. 1229-1312, a method of increasing accuracy of a recognition process targeting the special light image and the pigment-sprayed image is not disclosed.

In the method in accordance with the present embodiment, a recognition process of recognizing the region of interest (regions of interest) is performed using a trained model that is trained by having undergone pre-training that uses an image group including the normal light image, and then having undergone, after the pre-training, fine-tuning that uses an image group including the special light image or the pigment-sprayed image. This can increase recognition accuracy even in a case where the special light image and the pigment-sprayed image serve as targets of the recognition process. Note that the region of interest in accordance with the present embodiment is a region in which the order of priority in imaging for a user is relatively higher than that in other regions. In a case where the user is a doctor who performs diagnosis or treatment, the region of interest corresponds to, for example, a region that shows a lesion portion. Note that if a target on which the doctor wants to perform imaging is bubbles or feces, the region of interest may be a region that shows a bubble portion or a feces portion. That is, while a target to which the user should pay attention is different depending on a purpose of imaging, on the occasion of the imaging, a region where the order of priority in imaging for the user is relatively higher than that in the other regions is the region of interest.

First, an outline configuration of a system including an image processing system 200 in accordance with the present embodiment will be described below with reference to FIGS. 1 to 4. Thereafter, a specific method and the flow of processing will be described in first to third embodiments.

FIG. 1 illustrates a configuration example of the system including the image processing system 200. The system includes a training device 100, an image processing system 200, and an endoscope system 300. Note that a configuration of the system is not limited to that illustrated in FIG. 1. Various modifications can be made such as omission of part of constituent elements and addition of another constituent element.

The training device 100 performs machine learning to generate a trained model. The endoscope system 300 causes an endoscope imaging device to capture an in-vivo image. The image processing system 200 acquires the in-vivo image as a processing target image. The image processing system 200 then operates in accordance with the trained model generated by the training device 100 to perform a recognition process of recognizing a region of interest (regions of interest) targeting the processing target image. The endoscope system 300 acquires and displays a recognition result. This enables implementation of the system that supports the doctor's diagnosis and the like using the machine learning.

The training device 100, the image processing system 200, and the endoscope system 300, for example, may be arranged as individual devices. Each of the training device 100 and the image processing system 200 is, for example, an information processing device such as a personal computer (PC) and a server system. Note that the training device 100 may be implemented by a distributed process performed by a plurality of devices. For example, the training device 100 may be implemented by cloud computing using a plurality of servers. The image processing system 200 may be similarly implemented by cloud computing or the like. The endoscope system 300 is a device including an insertion section 310, a system control device 330, and a display section 340, as described later with reference to, for example, FIG. 4. Note that part or the whole of the system control device 330 may be implemented by equipment via a network of a server system or the like. For example, part or the whole of the system control device 330 is implemented by cloud computing.

In addition, one of the image processing system 200 and the training device 100 may include the other of the image processing system 200 and the training device 100. In this case, the image processing system (training device 100) is a system that performs machine learning to execute both the process of generating the trained model and the recognition process in accordance with the trained model. Alternatively, one of the image processing system 200 and the endoscope system 300 may include the other of the image processing system 200 and the endoscope system 300. For example, the system control device 330 of the endoscope system 300 includes the image processing system 200. In this case, the system control device 330 executes both control of each section of the endoscope system 300 and the recognition process in accordance with the trained model. Alternatively, a system including all of the training device 100, the image processing system 200, and the system control device 330 may be implemented. For example, a server system comprising one or more servers may perform the process of performing the machine learning to generate the trained model, the recognition process in accordance with the trained model, and control of each section of the endoscope system 300. As described above, the specific configuration of the system illustrated in FIG. 1 can be modified in various manners.

Figure 2:
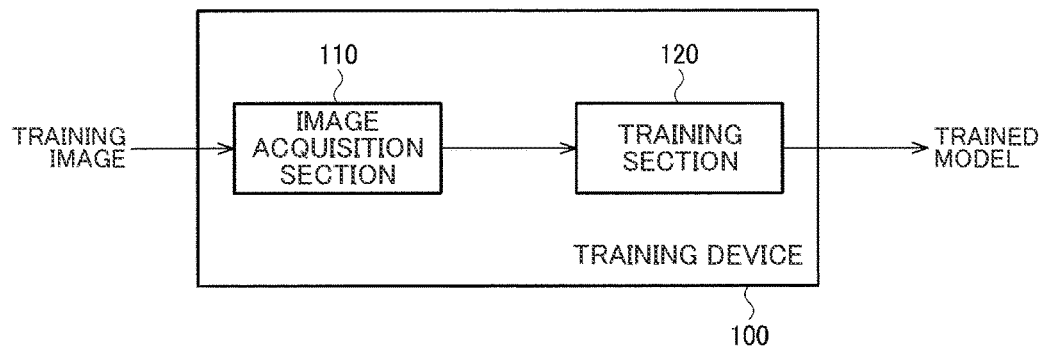
FIG. 2 illustrates a configuration example of a training device.

FIG. 2 illustrates a configuration example of the training device 100. The training device 100 includes an image acquisition section 110 and a training section 120. The image acquisition section 110 acquires a training image. The image acquisition section 110 is, for example, a communication interface for acquiring the training image from another device. The training image is, for example, an image in which the normal light image, the special light image, or the pigment-sprayed image is provided with ground truth (correct data) as metadata. The training section 120 performs machine learning based on the acquired training image to generate the trained model. Details of data used for the machine learning and the specific flow of the training process will be described later.

The training section 120 comprises the following hardware. The hardware can include at least one of a digital signal processing circuit or an analog signal processing circuit. For example, the hardware can comprise one or more circuit devices mounted on a circuit board, or one or more circuit elements. The one or more circuit devices are, for example, integrated circuits (ICs), field-programmable gate array (FPGA) circuits, or the like. The one or more circuit elements are, for example, resistors, capacitors, or the like.

In addition, the training section 120 may be implemented by the following processor. The training device 100 includes a memory that stores information, and a processor that operates based on the information stored in the memory. The information is, for example, a program and various kinds of data or the like. The processor includes hardware. Note that various kinds of processors such as a central processing unit (CPU), a graphics processing unit (GPU), and a digital signal processor (DSP) can be used. The memory may be a semiconductor memory such as a static random-access memory (SRAM) and a dynamic random-access memory (DRAM). The memory may be a register. The memory may be a magnetic storage device such as a hard disk drive (HDD). The memory may be an optical storage device such as an optical disk device. For example, the memory stores a computer-readable instruction. The instruction is executed by the processor, whereby a function of each section of the training section 120 is implemented as a processing. Each section of the training section 120 is, for example, each section described later with reference to FIGS. 7 and 12. The instruction mentioned herein may be an instruction of an instruction set that is included in a program, or may be an instruction that instructs a hardware circuit included in the processor to operate.

Figure 3:
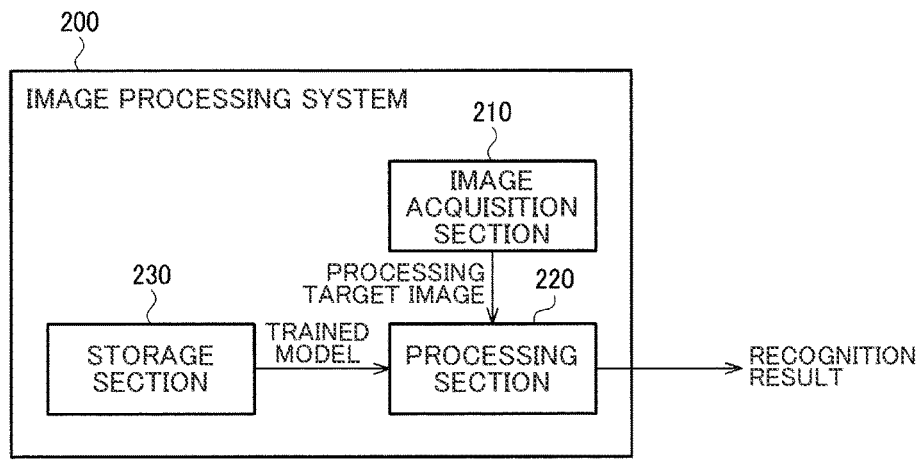
FIG. 3 illustrates a configuration example of the image processing system.

FIG. 3 illustrates a configuration example of the image processing system 200. The image processing system 200 includes an image acquisition section 210, a processing section 220, and a storage section 230.

The image acquisition section 210 acquires an in-vivo image captured by an imaging device of the endoscope system 300 as a processing target image. For example, the image acquisition section 210 is implemented as a communication interface that receives the in-vivo image via a network from the endoscope system 300. The network mentioned herein may be a private network such as an intranet, or may be a public telecommunication network such as the Internet. In addition, the network may be a wired network or a wireless network.

The processing section 220 operates in accordance with the trained model to perform the recognition process of recognizing the region of interest (regions of interest) in the processing target image. Additionally, the processing section 220 determines information to be output based on a result of recognition of the trained model. The processing section 220 comprises hardware including at least one of a digital signal processing circuit or an analog signal processing circuit. For example, the hardware can comprise one or more circuit devices mounted on a circuit board, or one or more circuit elements.

In addition, the processing section 220 may be implemented by the following processor. That is, the image processing system 200 includes a memory that stores information such as a program, and various kinds of data, and a processor that operates based on the information stored in the memory. The memory mentioned herein may be the storage section 230, or another different memory. Various kinds of processors such as a GPU can be used as the processor. The memory can be implemented in various manners such as a semiconductor memory, a resistor, a magnetic storage device, and an optical storage device. The memory stores a computer-readable instruction. The instruction is executed by the processor, whereby a function of each section of the processing section 220 is implemented. Each section of the processing section 220 is, for example, each section described later with reference to FIGS. 9 and 14.

The storage section 230 is a work area of the processing section 220 or the like, and the function thereof can be implemented by a semiconductor memory, a resistor, a magnetic storage device, or the like. The storage section 230 stores the processing target image acquired by the image acquisition section 210. Additionally, the storage section 230 stores information of the trained model generated by the training device 100.

Figure 4:
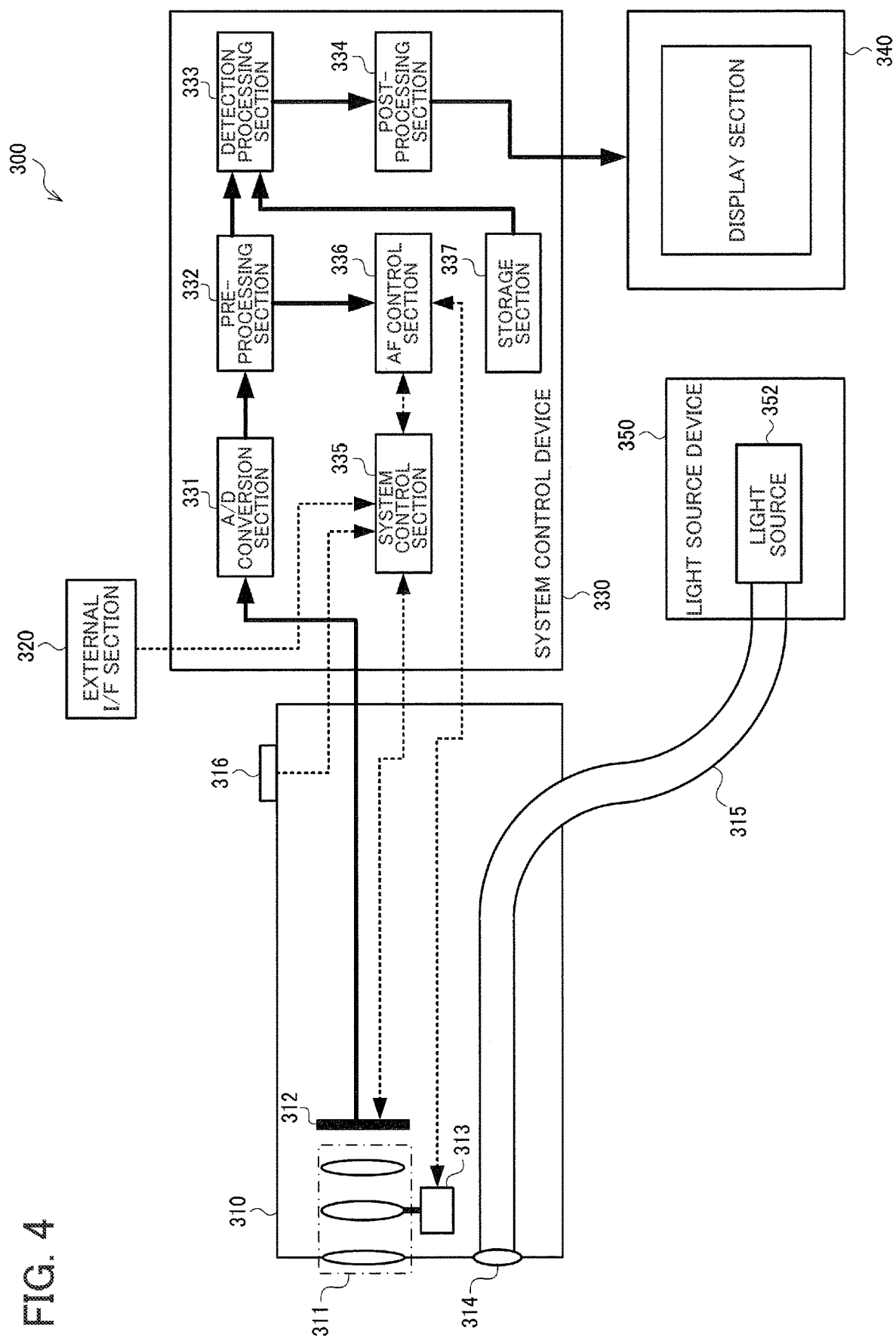
FIG. 4 illustrates a configuration example of an endoscope system.

FIG. 4 illustrates a configuration example of the endoscope system 300. The endoscope system 300 includes the insertion section 310, an external interface (I/F) section 320, the system control device 330, the display section 340, and a light source device 350.

The insertion section 310 is a portion whose distal end side is inserted into the body. The insertion section 310 includes an objective optical system 311, an image sensor 312, an actuator 313, an illumination lens 314, a light guide 315, and an auto focus (AF) start/end button 316.

The light guide 315 guides light emitted from a light source 352 to the distal end of the insertion section 310. The illumination lens 314 emits illumination light guided by the light guide 315 onto a subject. The objective optical system 311 receives reflected light from the subject and forms an image as a subject image. The objective optical system 311 includes a focus lens, and is capable of changing a position at which a subject image is formed in accordance with a position of the focus lens. The actuator 313 drives the focus lens based on an instruction from an AF control section 336. Note that AF is not essential, and the endoscope system 300 may have a configuration not including the AF control section 336.

The image sensor 312 receives light from the subject having passed through the objective optical system 311. The image sensor 312 may be a monochrome sensor, or may be an element having a color filter. The color filter may be a color filter in a well-known Bayer's arrangement, a complementary color filter, or another color filter. The complementary filter includes filters in respective colors of cyan, magenta, and yellow.

The AF start/end button 316 is an operation interface for a user to operate the start/end of AF. The external I/F section 320 is an interface by which the user performs an input operation to the endoscope system 300. The external I/F section 320 includes, for example, a button for setting an AF control mode, a button for setting an AF region, a button for adjusting an image processing parameter, and the like.

The system control device 330 performs image processing and control of the whole system. The system control device 330 includes an analog/digital (A/D) conversion section 331, a pre-processing section 332, a detection processing section 333, a post-processing section 334, a system control section 335, the AF control section 336, and a storage section 337.

The A/D conversion section 331 converts analog signals, which are sequentially output from the image sensor 312, to digital images, and sequentially outputs the digital images to the pre-processing section 332. The pre-processing section 332 performs various kinds of correction processes on in-vivo images sequentially output from the A/D conversion section 331, and sequentially outputs the in-vivo images to the detection processing section 333 and the AF control section 336. The correction processes include, for example, a white balance process, a noise reduction process, and the like.

The detection processing section 333, for example, performs a process of transmitting an image that has undergone the correction process and that is acquired from the pre-processing section 332 to the image processing system 200 arranged outside the endoscope system 300. The endoscope system 300 includes a communication section, which is not illustrated, and the detection processing section 333 performs communication control of the communication section. The communication section mentioned herein is a communication interface for transmitting an in-vivo image to the image processing system 200 via a given network. The detection processing section 333 performs communication control of the communication section to perform a process of receiving a recognition result from the image processing system 200.

Alternatively, the system control device 330 may include the image processing system 200. In this case, the A/D conversion section 331 corresponds to the image acquisition section 210. The storage section 337 corresponds to the storage section 230. The pre-processing section 332, the detection processing section 333, the post-processing section 334, and the like correspond to the processing section 220. In this case, the detection processing section 333 operates in accordance with the information of the trained model stored in the storage section 337 to perform the recognition process of recognizing the region of interest targeting the in-vivo image serving as the processing target image. In a case where the trained model is the neural network, the detection processing section 333 performs a calculation process in a forward direction using weight determined by training on the processing target image serving as an input. The detection processing section 333 then outputs a recognition result based on an output from an output layer.

The post-processing section 334 performs post-processing based on the recognition result from the detection processing section 333, and outputs an image having undergone the post-processing to the display section 340. As the post-processing mentioned herein, various kinds of processing such as highlighting of a recognition target in the image and addition of information indicating a detection result can be assumed. For example, the post-processing section 334 superimposes a detection frame detected in the detection processing section 333 on the image output from the pre-processing section 332 to perform post-processing to generate a display image.

The system control section 335 is connected to each of the image sensor 312, the AF start/end button 316, the external I/F section 320, and the AF control section 336, and controls each section. Specifically, the system control section 335 inputs/outputs various kinds of control signals. The AF control section 336 uses images sequentially output from the pre-processing section 332 to perform AF control.

The display section 340 sequentially displays images output from the post-processing section 334. The display section 340 is, for example, a liquid crystal display, an electro-luminescence (EL) display, or the like. The light source device 350 includes the light source 352 that emits illumination light. The light source 352 may be a xenon light source, a light emitting diode (LED), or a laser light source. Alternatively, the light source 352 may be another light source, and a light emission method is not specifically limited.

Note that the light source device 350 is capable of emitting normal light and special light. For example, the light source device 350 includes a white light source and a rotary filter, and is capable of switching between normal light and special light based on rotation of the rotary filter. Alternatively, the light source device 350 may have a configuration of including a plurality of light sources such as a red LED, a green LED, a blue LED, a green narrow band light LED, and a blue narrow band light LED, to be capable of emitting a plurality of types of light having different wavelength bands. The light source device 350 turns on the red LED, the green LED, and the blue LED to emit normal light, and turns on the green narrow band light LED and the blue narrow band light LED to emit special light. Note that various kinds of configurations of the light source device that emits normal light and special light are known, and a wide range of them is applicable to the present embodiment.

2. First Embodiment

First, an outline of the machine learning is described. The following description is given of the machine learning using the neural network, but the method in accordance with the present embodiment is not limited thereto. In the present embodiment, for example, machine learning using another model such as a support vector machine (SVM) may be performed, and machine learning using a method that has developed from various methods such as the neural network and the SVM may be performed.

Figure 5A:
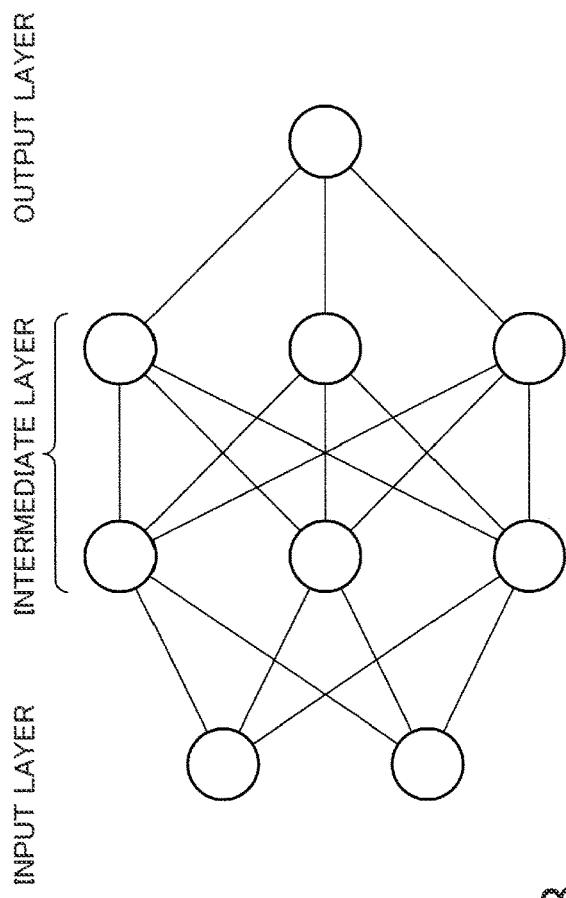
FIGS. 5A and 5B each illustrate a configuration example of a neural network.

FIG. 5A is a schematic diagram for describing the neural network. The neural network includes an input layer that takes input data, an intermediate layer that executes calculation based on an output from the input layer, and an output layer that outputs data based on an output from the intermediate layer. While FIG. 5A exemplifies a network having the intermediate layer comprising two layers, the intermediate layer may comprise one layer, or three or more layers. In addition, the number of nodes (neurons) included in each layer is not limited to that in the example of FIG. 5A, and can be modified in various manners. Note that in consideration of accuracy, the training in accordance with the present embodiment is preferably performed using deep learning using a multi-layer neural network. The multi-layer mentioned herein means four or more layers in a more limited sense.

As illustrated in FIG. 5A, a node included in a given layer is connected to a node in an adjacent layer. A weight coefficient is assigned between connected nodes. Each node multiplies an output from a node in a former stage by the weight coefficient and obtains a total value of results of multiplication. Furthermore, each node adds a bias to the total value and applies an activation function to a result of addition to obtain an output from the node. This process is sequentially executed from the input layer to the output layer, whereby an output from the neural network is obtained. Note that as the activation function, various functions such as a sigmoid function and a rectified linear unit (ReLU) function are known, and a wide range of these functions can be applied in the present embodiment.

The training in the neural network is a process of determining an appropriate weight coefficient. The weight coefficient mentioned herein includes a bias. Specifically, the training device 100 inputs input data out of training data to the neural network and performs calculation in the forward direction using the weight coefficient at this time to obtain an output. The training section 120 of the training device 100 performs calculation to obtain an error function based on the output and ground truth (correct data) out of the training data. The training section 120 updates the weight coefficient to make the error function smaller. In updating the weight coefficient, for example, backpropagation to update the weight coefficient from the output layer to the input layer can be utilized.

Figure 5B:

The neural network may be, for example, a convolutional neural network (CNN). FIG. 5B is a schematic diagram for describing the CNN. The CNN includes a convolution layer that performs convolution calculation and a pooling layer. The convolution layer is a layer that performs a filter process. The pooling layer is a layer that reduces a size in a vertical direction and a size in a lateral direction to perform pooling calculation. In the example illustrated in FIG. 5B, the CNN is a network that causes each of the convolution layer and the pooling layer to perform calculation a plurality of times, thereafter causes a fully connected layer to perform calculation, and thereby obtain an output. The fully connected layer is a layer that performs a calculation process in a case where all nodes included in the former layer are connected to corresponding nodes in the given layer, and the calculation process corresponds to calculation in each layer described above with reference to FIG. 5A. Note that FIG. 5B omits illustration of the calculation process with the activation function. Various kinds of configurations of the CNN have been known, and a wide range of these configurations are applicable to the present embodiment. For example, a known Region Proposal Network (RPN) or the like can be utilized as the CNN in accordance with the present embodiment.

In a case where the CNN is used, a procedure of processing is similar to that illustrated in FIG. 5A. That is, the training device 100 inputs input data, out of the training data, to the CNN, and performs a filter process or pooling calculation using filter characteristics at that time to obtain an output. The training device 100 calculates the error function based on the output and the ground truth, and updates the weight coefficient including the filter characteristics to make the error function smaller. For example, the backpropagation can be utilized also when the weight coefficient of the CNN is updated.

Subsequently, the machine learning in accordance with the present embodiment is described. The recognition process of recognizing the region of interest executed by the image processing system 200 includes a detection process of detecting at least one of detection data regarding at least one of whether the region of interest is present in an image, and, if any, a position, a size, and a shape of the region of interest, and a local classification process to differentiate a degree of malignancy of the region of interest.

For example, the detection process is a process of obtaining information that identifies a rectangular frame region surrounding the region of interest and a detection score representing a probability in the frame region. The frame region is hereinafter referred to as a detection frame. The information that identifies the detection frame is, for example, four numeric values comprising a coordinate value of an upper left end point of the detection frame on an abscissa axis, a coordinate value of the end point on an ordinate axis, a length of the detection frame in an abscissa axis direction, and a length of the detection frame in an ordinate axis direction. Since an aspect ratio of the detection frame changes with change of the shape of the region of interest, the detection frame corresponds to information indicating not only whether the region of interest is present, and, if any, the position and the size, but also the shape of the region of interest. Note that widely known segmentation may be used in the detection process in accordance with the present embodiment. In this case, with respect to each pixel in the image, information indicating whether or not the pixel is the region of interest, for example, information indicating whether or not the pixel corresponds to a polyp is output. In this case, it is possible to identify the shape of the region of interest in a more detailed manner.

The region of interest as the lesion is classified into several types depending on a degree of malignancy. For example, narrow-band imaging international colorectal endoscopic (NICE) classification to classify a polyp into Type 1 (benign), Type 2 (semimalignant), and Type 3 (malignant) has been widely known. A local classification process is a process of identifying which type the region of interest is. The local classification process in the present embodiment is not limited to processing in accordance with the NICE classification, and another classification may be used.

FIG. 6 is a diagram illustrating a configuration of a neural network in accordance with the present embodiment. As illustrated in FIG. 6, the neural network may include a feature amount extraction layer, a detection layer, and a local classification layer. Each rectangular region in FIG. 6 represents a layer that performs some kind of calculation in the convolution layer, the pooling layer, the fully connected layer, or the like. Note that the configuration of the CNN is not limited to that illustrated in FIG. 6, and may be modified in various manners.

The feature amount extraction layer accepts the processing target image as an input, performs calculation including convolution calculation, and thereby outputs a feature amount. The detection layer uses the feature amount output from the feature amount extraction layer as an input, and outputs information indicating a detection result. The local classification layer uses the feature amount output from the feature amount extraction layer as an input, and outputs information indicating a local classification result. The training device 100 executes a training process to determine a weight coefficient of each of the feature amount extraction layer, the detection layer, and the local classification layer.

Figure 7:
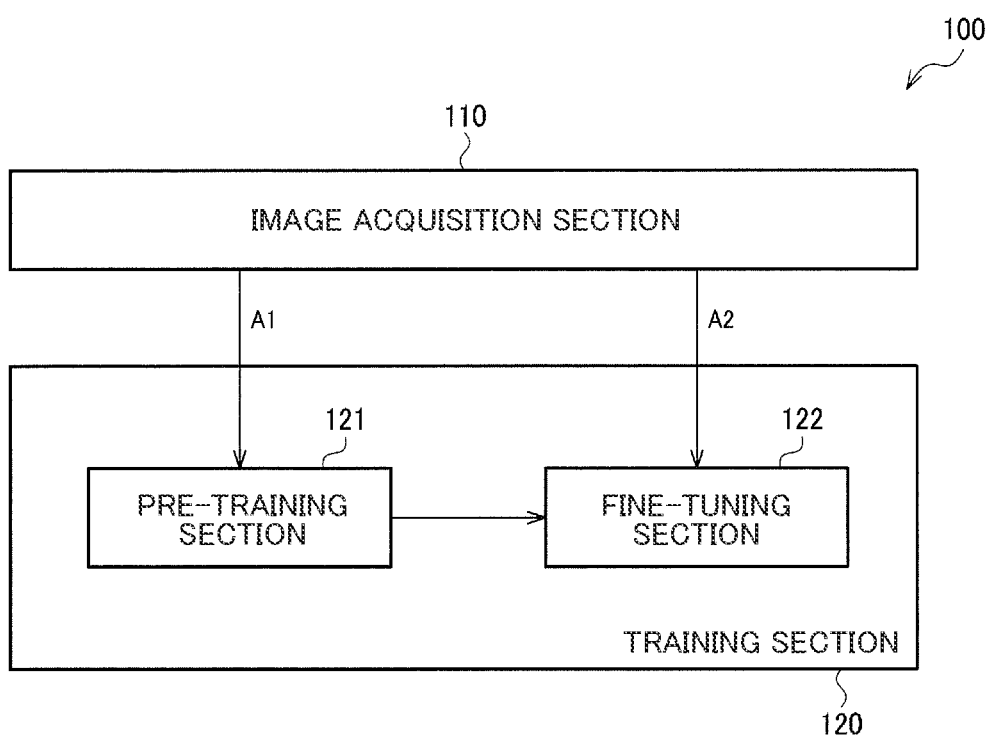
FIG. 7 illustrates a configuration example of a training device in accordance with a first embodiment.

FIG. 7 illustrates a configuration example of the training device 100 in accordance with a first embodiment. The training section 120 of the training device 100 includes a pre-training section 121 and a fine-tuning section 122. The pre-training section 121 acquires, as training data, an image group A1 from the image acquisition section 110, and performs pre-training based on the image group A1. The fine-tuning section 122 acquires, as training data, an image group A2 from the image acquisition section 110. The fine-tuning section 122 performs fine-tuning based on the image group A2 with the weight coefficient after the pre-training serving as an initial value.

The pre-training in accordance with the present embodiment is a training process that uses the normal light image that can be acquired in abundance. That is, the image group A1 is an image group including a plurality of training images in each of which the normal light image is provided with, as the ground truth, the detection data representing information regarding at least one of whether the region of interest is present, and, if any, the position, the size, and the shape of the region of interest. For example, the detection data is mask data in which a polyp region serving as a detection target and a background region are filled with different colors. Alternatively, the detection data may be information for identifying a detection frame surrounding a polyp.

As described above, the normal light observation is widely utilized in the step of searching for the region of interest. Thus, an abundance of normal light images provided with the detection data can be acquired, and thus the number of images included in the image group A1 is greater than that in the image group A2. For example, about hundreds of thousands of images are included in the image group A1, and several tens of thousands of images are included in the image group A2.

The pre-training section 121 performs pre-training that uses the image group A1. Specifically, the pre-training section 121 performs calculation in the forward direction based on a present weight coefficient with the normal light image included in the image group A1 serving as an input in the neural network illustrated in FIG. 6. The pre-training section 121 calculates, as an error function, an error between the output from the detection layer and the detection data serving as the ground truth, and performs a process of updating the weight coefficient so as to make the error function smaller. This is the process based on one training image, and the pre-training section 121 repeats the above-mentioned processing to execute pre-training. Note that the updating of the weight coefficient is not limited to the one performed on an image-by-image basis, and batch training or the like may be used.

Note that the calculation in the forward direction with the normal light image serving as the input also enables acquisition of an output from the local classification layer. However, since the ground truth in the image group A1 is the detection data corresponding to the detection result, the error function cannot be obtained from the output from the local classification layer and the ground truth. That is, in the pre-training, the weight coefficient of the feature amount extraction layer and the weight coefficient of the detection layer out of the neural network illustrated in FIG. 6 serve as targets of training.

The fine-tuning in accordance with the present exemplary embodiment is a training process that uses the special light images that are hard to be acquired in abundance. That is, the image group A2 is an image group including a plurality of training images in each of which the special light image is provided with, as the ground truth, the detection data and local classification data representing information that differentiates a degree of malignancy of the region of interest. The detection data is, for example, mask data similarly to the above-described example. The local classification data is, for example, label data representing any one of Type 1, Type 2, and Type 3 indicating a degree of malignancy of a polyp.

However, in a case where the normal light image captured with an observation method different from that of the special light image is input to the trained model having undergone fine-tuning that uses the special light image, there is a possibility that accuracy of the recognition process decreases. Hence, the image group A2 may include a plurality of training images in which the normal light image is provided with the detection data and the local classification data as the ground truth. That is, the image group A2 may be an image group including both the special light image and the normal light image. This enables generation of a versatile training model that can support both the normal light image and the special light image. Although it is not easy to acquire the normal light image provided with the local classification data in abundance, the normal light image is used for the fine-tuning herein so that there is no need for taking into consideration of decrease in accuracy due to insufficiency of the number of images. Note that the method in accordance with the present embodiment increases accuracy of the recognition process targeting the special light image that tends to be insufficient in number. For this reason, the configuration in which the image group A2 includes the normal light image is not essential.

The fine-tuning section 122 performs fine-tuning that uses the image group A2. Specifically, the fine-tuning section 122 performs calculation in the forward direction based on a present weight coefficient with the normal light image or the special light image included in the image group A2 serving as an input in the neural network illustrated in FIG. 6. The fine-tuning section 122 calculates, as the error function, an error between a result obtained by the calculation in the forward direction and the ground truth, and performs an updating process of updating the weight coefficient so as to make the error function smaller. For example, the fine-tuning section 122 obtains, as the error function, a weighted sum of an error between an output from the detection layer and the detection data and an error between an output from the local classification layer and the local classification data. That is, in the fine-tuning, the weight coefficient of the feature amount extraction layer, the weight coefficient of the detection layer, and the weight coefficient of the local classification layer out of the neural network illustrated in FIG. 6 each serve as a target of training.

Figure 8:
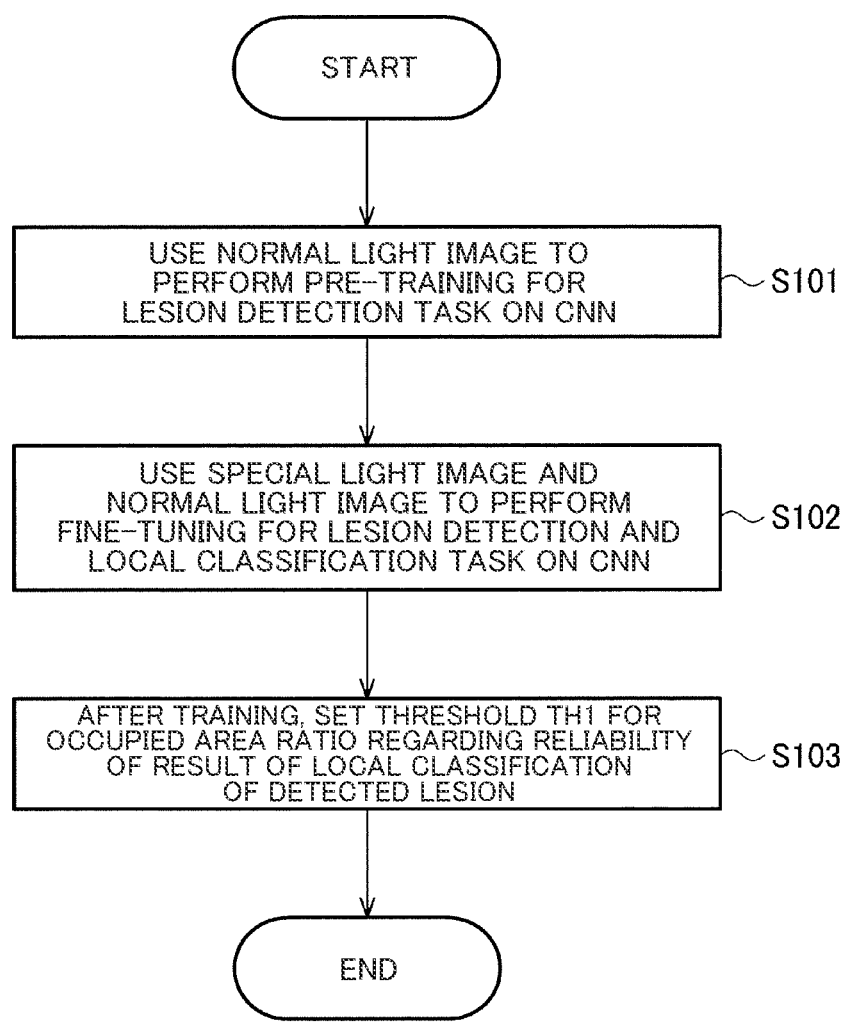
FIG. 8 is a flowchart describing a training process in accordance with the first embodiment.

FIG. 8 is a flowchart describing a training process in accordance with the first embodiment. When this process is started, in step S101, the pre-training section 121 uses the normal light image to perform pre-training for a lesion detection task on the CNN. The pre-training for the lesion detection task is a training process that uses the detection data as the ground truth to update the weight coefficient of the feature amount extraction layer and the weight coefficient of the detection data.

In step S102, the fine-tuning section 122 uses the special light image and the normal light image to perform fine-tuning for a lesion detection and local classification task on the CNN with a pre-training result serving as an initial value. The fine-tuning for the lesion detection and local classification task is a training process that uses both the detection data and the local classification data as the ground truth to update the weight coefficient of the feature amount extraction layer, the weight coefficient of the detection layer, and the weight coefficient of the local classification layer.

In step S103, the training device 100 sets a threshold TH1 for an occupied area ratio regarding reliability of a result of local classification of a detected lesion. As for a method of setting the threshold TH1, for example, validation data is prepared in advance, and the threshold TH1 is set so that a classification error rate of the validation data is equal to or less than 10%. The validation data is, for example, a training image that is not used for the fine-tuning out of the image group A2, and represents data in which the normal light image or the special light image is provided with the detection data and the local classification data. Since the validation data is data provided with the ground truth, using the validation data enables evaluation of a classification error rate of the trained model.

2.2 Recognition Process

Figure 9:
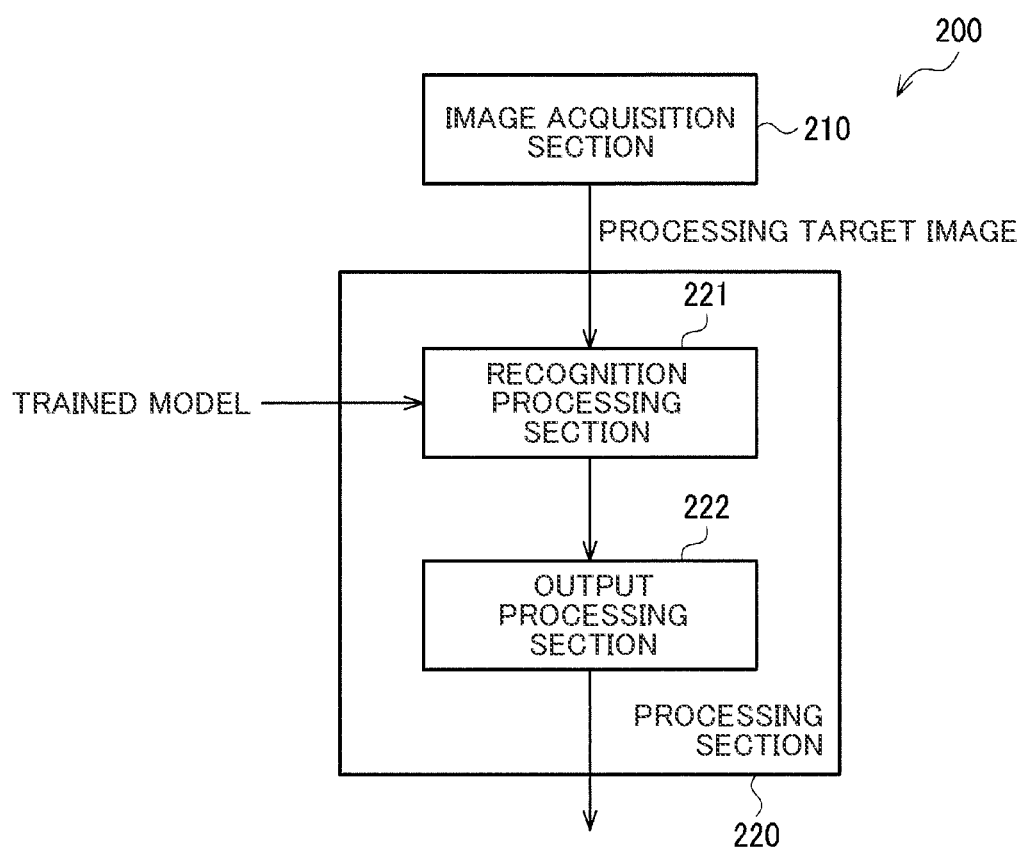
FIG. 9 illustrates a configuration example of an image processing system in accordance with the first embodiment.

FIG. 9 illustrates a configuration example of the image processing system 200 in accordance with the first embodiment. The processing section 220 of the image processing system 200 includes a recognition processing section 221 and an output processing section 222. The recognition processing section 221 operates in accordance with the trained model generated by the training device 100. The output processing section 222 performs an output process based on a calculated result from the trained model.

Figure 10:
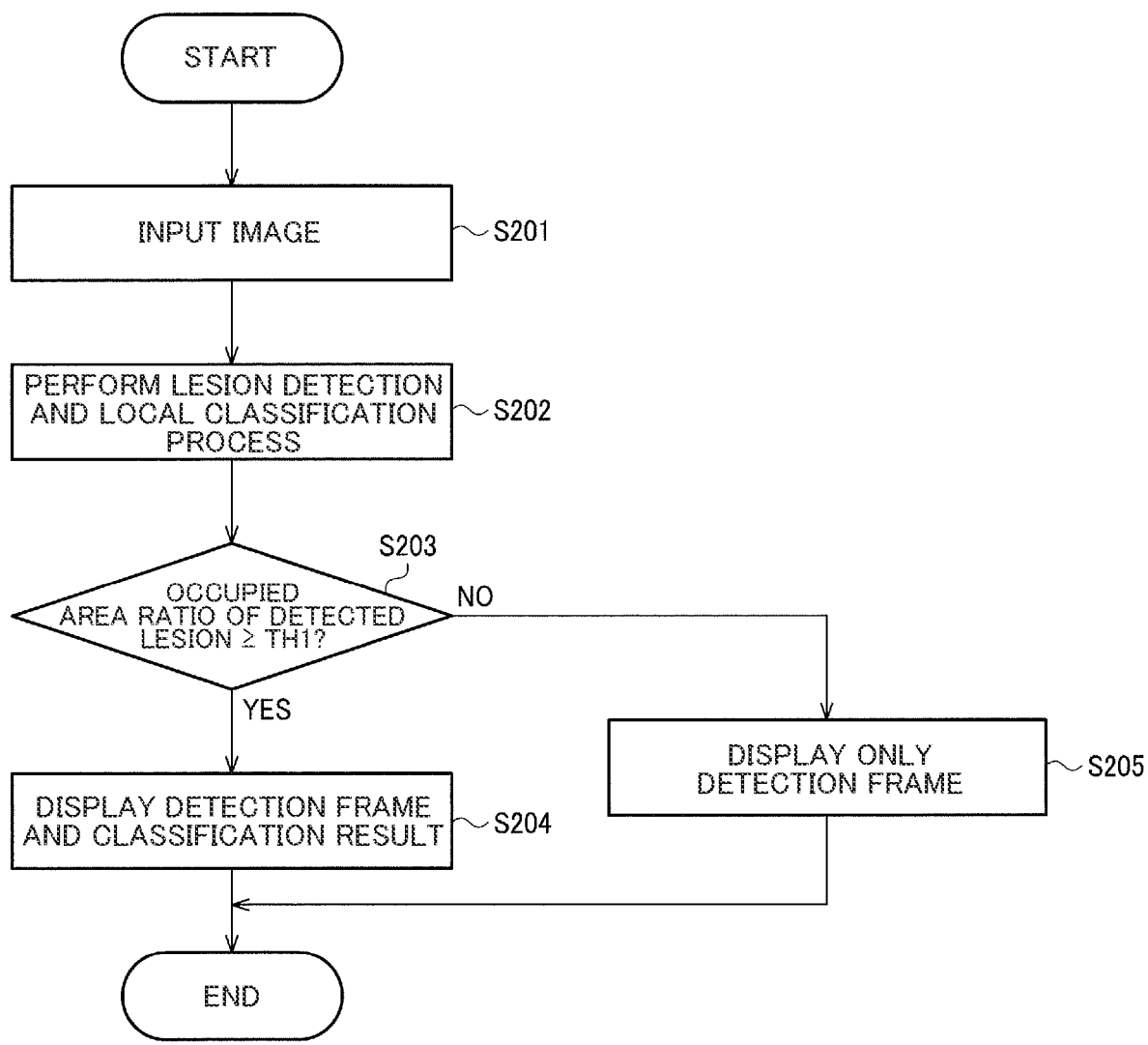
FIG. 10 is a flowchart describing a recognition process in accordance with the first embodiment.

FIG. 10 is a flowchart describing processing of the image processing system 200 in accordance with the first embodiment. First, in step S201, the image acquisition section 210 acquires an in-vivo image captured by the endoscope imaging device as a processing target image.

In steps S202, the recognition processing section 221 performs calculation in the forward direction with the processing target image acquired by the image acquisition section 210 serving as the input to the trained model. In processing in step S202, the recognition processing section 221 acquires information indicating a detection result from the detection layer and information indicating a local classification result from the local classification layer.

For example, the recognition processing section 221 acquires information regarding a position and size of each of a predetermined number of detection frames in the processing target image, a detection score associated with each detection frame, a local classification label, and a local classification score. The detection result in the present embodiment represents, for example, the detection frame, and the detection score represents a probability of the detection result. Specifically, the detection score is numeric value data representing a probability that the detection frame is a region surrounding the region of interest. The local classification result in the present embodiment represents, for example, the local classification label, and the local classification score is information indicating a probability of the local classification result. In a case where the NICE classification is used, an output from the local classification layer includes a numeric value representing a probability that a polyp corresponding to the detection frame is Type 1, and a numeric value representing a probability that the polyp corresponding to the detection frame is Type 2, and a numeric value representing a probability that the polyp corresponding to the detection frame is Type 3. For example, in a case where the output layer of the local classification layer is a known softmax layer, the local classification layer outputs three pieces of probability data, a total value of which is 1. The local classification label is information that identifies a type having the highest probability data out of Types 1 to 3. The local classification score is, for example, the highest value out of the three pieces of probability data.

Subsequently, the output processing section 222 generates output information based on the detection frame, the detection score, the local classification label, and the local classification score. For example, the output processing section 222 may perform pre-processing, which is not illustrated, to compare the detection score and a given detection threshold TH2. In a case where the detection score of a given detection frame is less than the detection threshold TH2, information regarding the detection frame has low reliability, and is thus excluded from an output target. Alternatively, the recognition processing section 221 may be configured not to transmit a detection frame having a detection score that is less than the TH2 to the output processing section 222.

In step S203, the output processing section 222 determines whether an occupied area ratio of the region of interest in an image is equal to or greater than the threshold TH1 that has been set in advance. For example, the output processing section 222 sets an area ratio of the detection frame to the whole of the processing target image as the occupied area ratio. If a determination result in step S203 is true, in step S204, the output processing section 222 performs a process of outputting the detection frame and the local classification label. If the determination result in step S203 is false, in step S205, the output processing section 222 performs a process of outputting only the detection frame. Note that the output processing section 222 may output the detection frame to which the detection score is added, or output the local classification label to which the local classification score is added. This enables presentation of reliability of information to a user.

In a case where the image processing system 200 is included in the endoscope system 300, the processing in step S204 or S205 is, for example, a process of generating a display image, and a process of displaying the display image on the display section 340. In a case where the image processing system 200 and the endoscope system 300 are arranged as individual devices, the above-mentioned processing is, for example, a process of transmitting the display image to the endoscope system 300. Alternatively, the above-described processing may be a process of transmitting the information indicating the detection frame and the local classification label to the endoscope system 300. In this case, each of the process of generating the display image and the display control is executed in the endoscope system 300.

As described above, the image processing system 200 in accordance with the present embodiment includes the image acquisition section 210 that acquires, as the processing target image, the in-vivo image captured by the endoscope imaging device, and the processing section 220 that operates in accordance with the trained model to perform the process of outputting the recognition result representing a result of recognition of the region of interest in the processing target image. The endoscope imaging device mentioned herein is an imaging device that is arranged in the endoscope system 300 and that is capable of outputting a result of formation of a subject image corresponding to the living body, and corresponds to the image sensor 312 in a more limited sense.

The trained model in accordance with the present embodiment is trained by having undergone pre-training that uses a first image group including images captured in a first observation method, and then having undergone, after the pre-training, fine-tuning that uses a second image group including images captured in a second observation method, as well as that uses ground truth regarding the region of interest included in the second image group. The first image group corresponds to the image group A1 illustrated in FIG. 7, and the second image group corresponds to the image group A2.

The first observation method mentioned herein is an observation method that uses normal light as illumination light. The second observation method is an observation method that uses special light as the illumination light. The second image group includes at least one image captured with the region of interest, and the second image group is lesser in number of images than the first image group.

In accordance with the method of the present embodiment, the pre-training of the machine learning using the normal light image captured in the normal light observation is performed to supplement insufficiency of the number of training images captured in the special light observation. In a case where the neural network is used, the pre-training is a process of setting an initial value of the weight coefficient used when the fine-tuning is performed. This can increase accuracy of the recognition process targeting the special light image as compared with a case where the pre-training is not performed.

Note that calculation in accordance with the trained model in the processing section 220, that is, calculation for outputting output data based on input data may be executed by software, or hardware. In other words, product-sum calculation executed at each node in FIG. 5A, a filter process executed in the convolution layer of the CNN, or the like may be executed by software. Alternatively, the above-mentioned calculation may be executed by a circuit device such as a FPGA circuit. Still alternatively, the above-mentioned calculation may be executed by software and hardware in combination. In this manner, operations of the processing section 220 in accordance with an instruction from the trained model can be implemented in various manners. For example, the trained model includes an inference algorithm, and a parameter used in the inference algorithm. The inference algorithm is an algorithm that performs filter calculation or the like based on the input data. The parameter is a parameter acquired by a training process, and is, for example, a weight coefficient. In this case, both the inference algorithm and the parameter are stored in the storage section 230, and the processing section 220 may read out the inference algorithm and the parameter and thereby perform the inference process with software. Alternatively, the inference algorithm may be implemented by the FPGA circuit or the like, and the storage section 230 may store the parameter. Still alternatively, the inference algorithm including the parameter may be implemented by the FPGA circuit or the like. In this case, the storage section 230 that stores information of the trained model is, for example, a built-in memory of the FPGA circuit.

Figure 11:
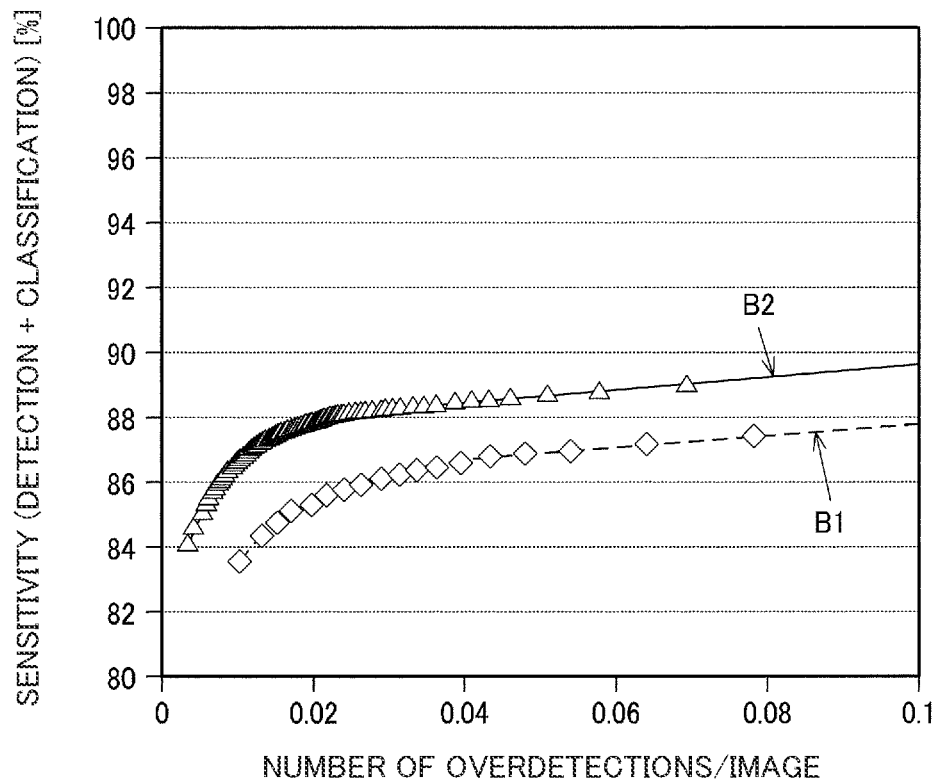
FIG. 11 is a diagram for describing an effect in accordance with the present embodiment.

FIG. 11 is a diagram for describing an effect in accordance with the present embodiment. An abscissa axis in FIG. 11 represents the number of overdetections per image. The number of overdetections is the number of erroneous detections of a region that is not a polyp. An ordinate axis represents sensitivity. The sensitivity represents a ratio of polyps that can be appropriately detected and from which appropriate local classification results are obtained, out of polyps whose images are captured in images used for validation.

B1 in FIG. 11 represents a sensitivity graph in a case where training is performed with only the image group in which the special light image is provided with the detection data (mask data) and the local classification data (classification label) serving as the training data. B2 represents a sensitivity graph in a case where pre-training is performed using the image group in which the normal light image is provided with the mask data, and thereafter fine-tuning is performed using the image group in which the special light image is provided with the mask data and the classification label.

As can be seen from FIG. 11, B2 shows increased sensitivity in detection and local classification as compared with B1. That is, the method in accordance with the present embodiment can increase accuracy of object recognition in the special light image. Since each of the pre-training and the fine-tuning is performed using the in-vivo image in the method in accordance with the present embodiment, domain adaptation when transfer learning is performed by the fine-tuning works better than a case where the pre-training is performed with an image group of images of general objects such as ImageNet.

Note that FIG. 11 illustrates an example of result of inputting the special light image to the CNN having undergone the fine-tuning that uses the special light image. However, as described above, one CNN model may undergo the fine-tuning with mixture of the normal light image and the special light image. In this case, it is possible to construct a system capable of performing differentiation/diagnosis support in either case where the normal light image is input to the CNN, or the special light image is input to the CNN.

The description has been given of the example in which the second observation method is an observation method that uses special light as illumination light. Note that the second observation method may be an observation method in which a pigment has been sprayed onto a subject. Specific processing is similar to that of the example of the special light image, and the special light image described above can be replaced with the pigment-sprayed image.

In addition, the region of interest in accordance with the present embodiment may be a polyp. This enables execution of the detection process targeting the polyp and the local classification process with high accuracy. When a degree of malignancy of the polyp is differentiated, the special light observation such as the NBI or the pigment spray observation has been widely used. For this reason, the method in accordance with the present embodiment capable of increasing accuracy of processing using the special light image or the pigment-sprayed image has good compatibility with the recognition process of the polyp.

The ground truth provided to the second image group in the present embodiment is data including at least one of the detection data regarding at least one of whether the region of interest is present in the image, and, if any, the position, the size, and the shape of the region of interest, and local classification data indicating the degree of malignancy of the region of interest in the image. The recognition result obtained by the processing section 220 of the image processing system 200 includes the detection result regarding at least one of whether the region of interest is present in the image, and, if any, the position, the size, and the shape of the region of interest, and the local classification result regarding the degree of malignancy of the region of interest in the image.

This enables execution of at least one of the detection process or the local classification process (differentiation process) as the recognition process. The above description has been given of the example in which the recognition process is both the detection process and the local classification process. This enables differentiation of the degree of malignancy, in addition to detection of the position, the size, or the like of the region of interest such as the polyp. Since it is possible to present at which position the polyp exists in the image and how much degree of malignancy of the polyp is, it is possible to appropriately support the user's diagnosis or the like.

However, the trained model in accordance with the present embodiment may output only the detection result, or may output only the local classification result. For example, in a case where the special light image is used for a purpose of screening, it is only required to acquire the detection result. If the position or the like of the region of interest is known by screening performed in advance, it is only required to acquire the local classification result in imaging using the special light image.

In addition, the processing section 220 in accordance with the present embodiment outputs, instead of outputting the detection result and the local classification result acquired by the trained model as they are, only results that satisfy a predetermined condition. For example, as described above, the recognition result to be output may be limited to a result having the detection score that is equal to or greater than the given threshold TH2. This can prevent information having low reliability from being output, and thereby enables appropriate support for the user's diagnosis or the like. Furthermore, the output of the local classification label may be limited to a label for which an area of the region of interest is equal to or greater than the given threshold TH1. Although detection itself of a polyp that is small in size in the image is possible, sufficient information regarding a fine structure is not acquired, and thus such a polyp is not appropriate for differentiation of the degree of malignancy of the polyp. As illustrated in FIG. 6, the neural network in accordance with the present embodiment performs calculation in the forward direction with the processing target image serving as the input, and thereby acquires the local classification label. However, in a case where the area of the region of interest is small, the reliability of the local classification label is low. In this regard, determining whether or not the area of the region of interest is equal to or greater than the threshold TH1 can prevent the information having low reliability from being output.

Note that the process of determining information to be output is not limited to the process of using the area of the region of interest, and can be modified in various manners. For example, the processing section 220 obtains, based on the trained model, the detection score representing a degree of probability of the detection result and the local classification score representing a degree of probability of the local classification. In a case where the detection score is greater than a given detection threshold, the processing section 220 may output the detection score. In a case where the local classification score is greater than a given classification threshold, the processing section 220 may output the local classification result.

The local classification score is, for example, the highest value out of pieces of probability data corresponding to the respective types of Type 1 to Type 3 as described above. For example, consideration is given to a case where the probability data of Type 1 is 0.4, the probability data of Type 2 is 0.3, and the probability data of Type 3 is 0.3. In this case, since a type having the highest probability data is Type 1, the local classification label indicates "Type 1". However, the local classification score representing a probability of Type 1 is as small as 0.4, and there is a small difference between the probability of Type 1 and a probability of Type 2 or a probability of Type 3. Thus, the local classification label indicating "Type 1" has low reliability. For this reason, in a case where the local classification score is less than the classification threshold, the output processing section 222 does not output the local classification result. The classification threshold can be set in various manners, and is, for example, a value greater than 0.5. This can prevent information having low reliability from being output based on the local classification score.

Alternatively, the processing section 220 may determine, based on the detection result, whether or not a condition regarding at least one of the size of the region of interest, blur, or motion blur is satisfied. In a case where the condition is satisfied, the processing section 220 outputs the detection result and the local classification result. In a case where the condition is not satisfied, the processing section 220 outputs the detection result without outputting the local classification result.

The condition regarding the size of the region of interest mentioned herein is, for example, the above-mentioned condition that the occupied area ratio is equal to or greater than the threshold TH1. This can prevent the local classification result from being output in a case where the region of interest is small to a degree of being inappropriate for differentiation.

The condition regarding the blur is, for example, a condition that an amount of blur is equal to or less than a blur threshold. The condition regarding the motion blur is, for example, a condition that an amount of motion blur is equal to or less than a motion blur threshold. In a case where the amount of blur or the amount of motion blur is large, for example, information regarding a fine structure of the region of interest such as an edge is lost. Thus, such a case is not appropriate for differentiation. In this manner, determining the condition regarding blur or motion blur can prevent information having low reliability from being output.

The amount of blur mentioned herein is an index representing a degree of blur. The blur represents that an image is blurred because the subject is out of focus. For example, the output processing section 222 performs an image process to provide the processing target image with a predetermined amount of blur, and thereafter performs a process of comparing the processed image and an original image. In a case where an amount of blur of the original image is small, there is a large difference in degree of blur between the images. On the other hand, in a case where the amount of blur of the original image is large in the first place, a change made by the image process is small and a difference in degree of blur between the images becomes small. The output processing section 222 is capable of calculating an amount of blur based on the comparison between the two images.

The amount of motion blur is an index representing a degree of motion blur. The motion blur represents that an image is blurred because the subject is moved relative to an imaging device. In the in-vivo image captured in the endoscope system 300, illumination light is regularly reflected on the subject, whereby an image of a bright spot is captured. The bright spot is a region where luminance is relatively high, and corresponds to, for example, an overexposure region. In a case where motion blur is small, the bright spot has a circular shape, or a shape similar to the circular shape. On the other hand, in a case where motion blur becomes large, the bright spot becomes to have a shape extending in a moving direction due to the relative movement between the subject and the imaging device. The output processing section 222 is capable of calculating an amount of motion blur based on the shape of the bright spot.

Note that determination may be made with respect to any one of the conditions regarding the size, the blur, and the motion blur, or determination may be made with respect to a combination of two or more of the conditions. Assume a case where the two or more conditions are combined. When all of the conditions are satisfied, the detection result and the local classification result are output. When at least one condition is not satisfied, only the detection result is output. Note that a way of combining a plurality of conditions can be modified in various manners.

The trained model in accordance with the present embodiment comprises a CNN. This enables efficient and highly accurate execution of the recognition process with an image serving as an input. Note that as the CNN that performs object recognition, various methods, such as, besides a method of a Region Based Convolutional Neural Networks (R-CNN) and a method that has been developed from the R-CNN, You Only Look Once (YOLO) and Single Shot Detector (SSD), have been known, and a wide range thereof can be applied to the present embodiment.

The trained model in accordance with the present embodiment may include, as illustrated in FIG. 6, the feature amount extraction layer that outputs the feature amount based on the processing target image, the detection layer that outputs the detection result based on the feature amount, and the local classification layer that outputs the local classification result based on the feature amount. Performing pre-training that uses the first image group including the image provided with the detection data as the ground truth trains the model in the weight coefficient of the feature amount extraction layer and the weight coefficient of the detection layer. Performing fine-tuning that uses the second image group including the image provided with the detection data and the local classification data as the ground truth trains the model in the weight coefficient of the feature amount extraction layer, the weight coefficient of the detection layer, and the weight coefficient of the local classification layer.

The usage of the configuration illustrated in FIG. 6 enables commonality of extraction of the feature amount in the detection process and extraction of the feature amount in the local classification process. For this reason, it is possible to reduce the size of the trained model as compared with a case where the feature amount extraction layer is arranged in each of the detection process and the local classification process. For example, in a case where the storage section 230 of the image processing system 200 stores the weight coefficients of the trained model, it is possible to reduce capacity of the storage section 230. Alternatively, in a case where an inference process algorithm in accordance with the trained model comprises the FPGA circuit or the like, it is possible to reduce the size of the FPGA circuit.

In addition, the method in accordance with the present embodiment can be applied to the training device 100. The training device 100 includes the image acquisition section 110 and the training section 120. The image acquisition section 110 acquires the first image group including images captured in the first observation method and the second image group including images captured in the second observation method. The training section 120 performs pre-training that uses the first image group, then performs, after the pre-training, fine-tuning that uses the second image group, as well as that uses the ground truth regarding the region of interest included in the second image group, and thereby generates the trained model. The trained model is a model that outputs, when the processing target image is input thereto, the recognition result representing a result of recognition of the region of interest in the processing target image. The first observation method is an observation method that uses normal light as illumination light. The second observation method is an observation method that uses special light as the illumination light or an observation method in which a pigment has been dispersed onto the subject. The second image group includes at least one image captured with the region of interest, and is lesser in number of images than the first image group.

This enables generation of the training model capable of executing the recognition process of recognizing the region of interest targeting the special light image or the pigment-sprayed image with high accuracy.

The processing executed by the training device 100 in accordance with the present embodiment may be implemented as a training method. The training method in accordance with the present embodiment is a method of acquiring the first image group including images captured in the first observation method and the second image group including images captured in the second observation method, performing pre-training that uses the first image group, then performing, after the pre-training, fine-tuning that uses the second image group, as well as that uses the ground truth regarding the region of interest trained model included in the second image group, and thereby generating the trained model that outputs, when the processing target image is input thereto, the recognition result representing a result of recognition of the region of interest in the processing target image. The first observation method is an observation method that uses normal light as illumination light. The second observation method is an observation method that uses special light as the illumination light or an observation method in which a pigment has been sprayed onto the subject.

3. Second Embodiment

3.1 Training Process

In the first embodiment, the description has been given of the method in which the training device 100 generates one trained model, the image processing system 200 performs the recognition process of recognizing the region of interest targeting at least one of the special light image or the pigment-sprayed image based on the one trained model. However, the recognition process in accordance with the present embodiment may be performed using a plurality of trained models. Note that also in a second embodiment, a description will be given of an example in which the second observation method is the special light observation, but the second observation method may be the pigment spray observation. That is, in the following description, the special light observation or the special light image can be replaced with the pigment spray observation and the pigment-sprayed image, respectively, where appropriate.

Figure 12:
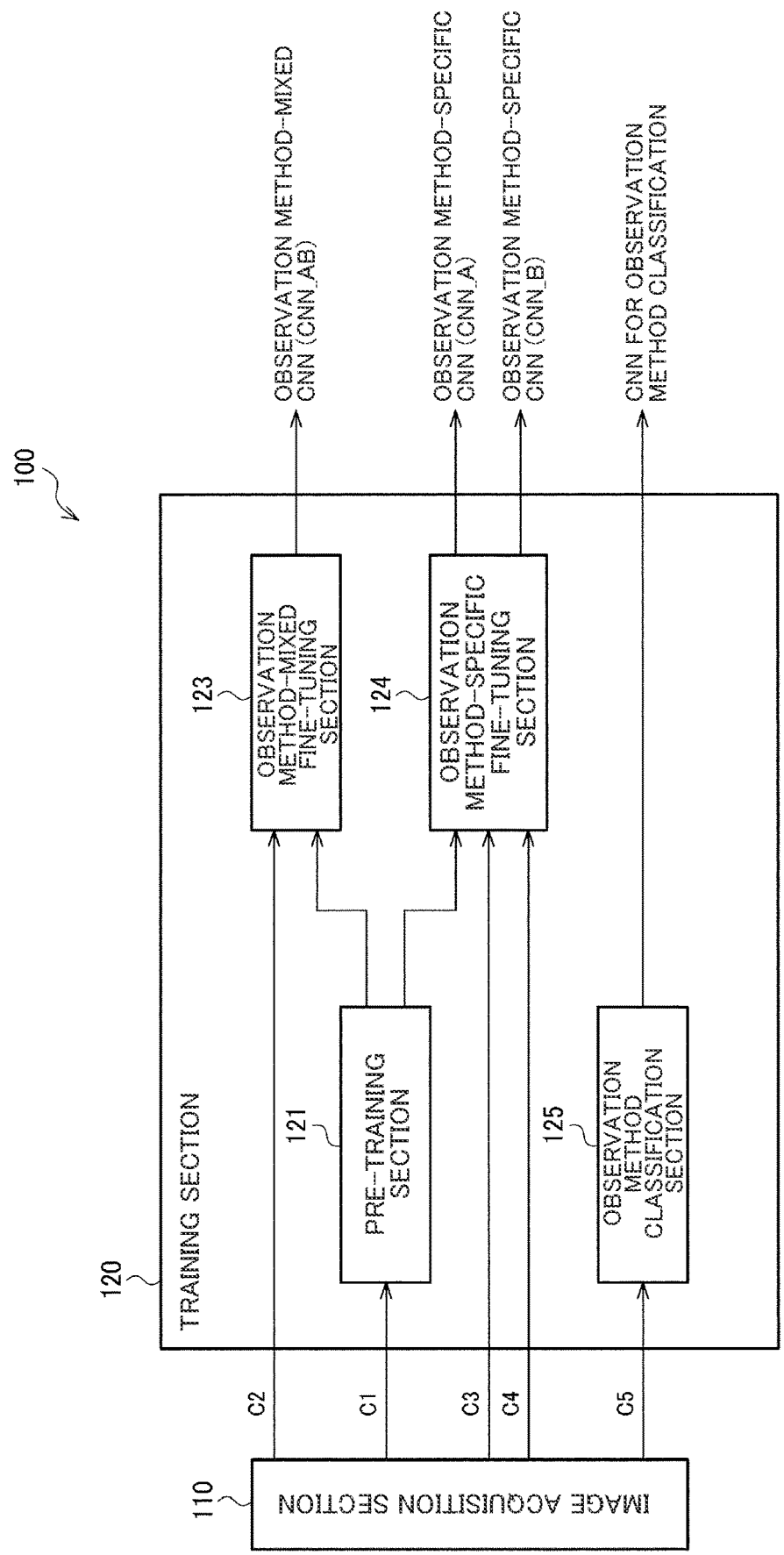
FIG. 12 illustrates a configuration example of a training device in accordance with a second embodiment.

FIG. 12 illustrates a configuration example of the training device 100 in accordance with the second embodiment. The training section 120 of the training device 100 includes the pre-training section 121, an observation method-mixed fine-tuning section 123, an observation method-specific fine-tuning section 124, and an observation method classification section 125.

The pre-training section 121 acquires an image group C1 from the image acquisition section 110, and performs pre-training based on the image group C1.

The observation method-mixed fine-tuning section 123 acquires an image group C2 from the image acquisition section 110. The observation method-mixed fine-tuning section 123 performs fine-tuning based on the image group C2 with the weight coefficient after the pre-training serving as an initial value.

The observation method-specific fine-tuning section 124 acquires image groups C3 and C4 from the image acquisition section 110. The observation method-specific fine-tuning section 124 performs fine-tuning based on the image group C3 with the weight coefficient after the pre-training serving as an initial value. The observation method-specific fine-tuning section 124 performs fine-tuning based on the image group C4 with the weight coefficient after the pre-training serving as an initial value. That is, the observation method-specific training section 124 generates a plurality of trained models based on a plurality of different image groups.

The observation method classification section 125 acquires an image group C5 from the image acquisition section 110, and performs machine learning based on the image group C5. The machine learning in the observation method classification section 125 is, for example, full-training that is not classified as the pre-training or the fine-tuning.

The pre-training in accordance with the present embodiment is similar to that in the first embodiment. That is, the image group C1 is, similarly to the image group A1, an image group including a plurality of training images in each of which the normal light image is provided with the detection data as the ground truth. The pre-training section 121 performs training of the weight coefficient of the feature amount extraction layer and the weight coefficient of the detection layer out of the neural network illustrated in FIG. 6, similarly to the first embodiment.

The fine-tuning executed in the observation method-mixed fine-tuning section 123 is a training process for generating a versatile trained model that is applicable to both the normal light image and the special light image. That is, the image group C2 includes a training image in which the normal light image is provided with the detection data and the local classification data, and a training image in which the special light image is provided with the detection data and the local classification data. In the observation method-mixed fine-tuning section 123, the weight coefficient of the feature amount extraction layer, the weight coefficient of the detection layer, and the weight coefficient of the local classification layer in the neural network illustrated in FIG. 6 each serve as a target of training. The observation method-mixed fine-tuning section 123 outputs an observation method-mixed CNN as the trained model. The observation method-mixed CNN is hereinafter referred to as CNN_AB.

The fine-tuning executed in the observation method-specific fine-tuning section 124 is a training process for generating a trained model dedicated to either the normal light image or the special light image. That is, the image group C3 includes a training image in which the normal light image is provided with the detection data and the local classification data. The image group C3 does not include a training image in which the special light image is provided with the detection data and the local classification data, or even if the image group C3 includes the training image, training images are sufficiently lesser in number than normal light images. That is, the observation method-specific fine-tuning section 124 uses the image group C3 to perform training of all of the weight coefficient of the feature amount extraction layer, the weight coefficient of the detection layer, and the weight coefficient of the local classification layer in the neural network illustrated in FIG. 6. The observation method-specific fine-tuning section 124 outputs an observation method-specific CNN appropriate for the normal light observation as the trained model. The observation method-specific CNN is hereinafter referred to as CNN_A.

Similarly, the image group C4 includes a training image in which the special light image is provided with the detection data and the local classification data. The image group C4 does not include a training image in which the normal light image is provided with the detection data and the local classification data, or even if the image group C4 includes the training image, training images are sufficiently lesser in number than special light images. That is, the observation method-specific fine-tuning section 124 uses the image group C4 to perform training of all of the weight coefficient of the feature amount extraction layer, the weight coefficient of the detection layer, and the weight coefficient of the local classification layer in the neural network illustrated in FIG. 6. The observation method-specific fine-tuning section 124 outputs an observation method-specific CNN appropriate for the special light observation as the trained model. The observation method-specific CNN appropriate for the special light observation is hereinafter referred to as CNN_B.

As described above, in the second embodiment, three CNNs each having the configuration illustrated in FIG. 6, and training of the weight coefficients of the respective CNNs is performed by individual fine-tuning that uses different image groups. That is, the three trained models CNN_A, CNN_B, and CNN_AB having different weight coefficients are generated.

The image group C5 is an image group including a training image in which the normal light image is provided with, as the ground truth, observation method data representing information that identifies an observation method, and a training image in which the special light image is provided with the observation method data. The observation method classification section 125 performs machine learning of the model including an input layer that takes an input image and an output layer that outputs a result of observation method classification. A configuration of an intermediate layer of the model can be modified in various manners.

Note that the result of observation method classification includes, for example, data representing a probability that the input image is the normal light image captured in the normal light observation and data representing a probability that the input image is the special light image captured in the special light observation. The observation method classification section 125 performs calculation in the forward direction based on a present weight coefficient with the normal light image or the special light image included in the image group C5 serving as an input. The observation method classification section 125 calculates, as an error function, an error between the result of observation method classification obtained by the calculation in the forward direction and the observation method data as the ground truth, and performs an updating process of updating the weight coefficient so as to make the error function smaller. With this processing, the observation method classification section 125 generates a trained model for identifying an observation method of the input image. The trained model for identifying the observation method is hereinafter referred to as a CNN for observation method classification.

Note that as described later, the trained model may not be used in an observation method classification process in the image processing system 200. In this case, the observation method classification section 125 can be omitted.

Figure 13A:
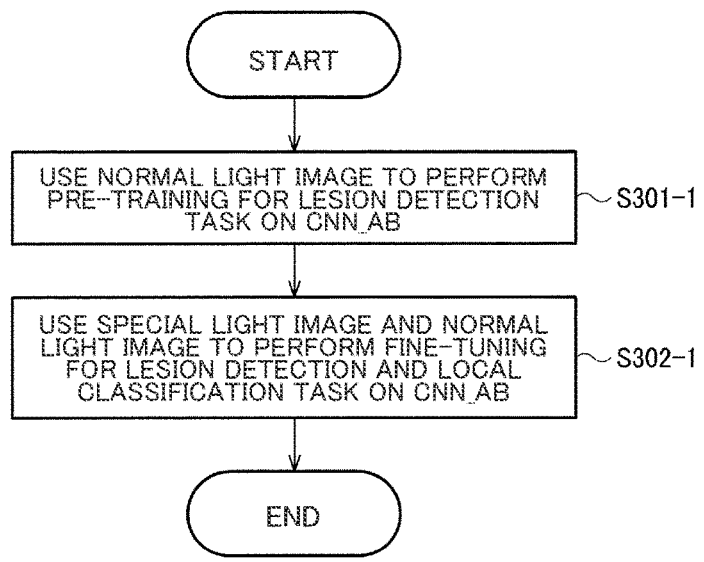
FIGS. 13A to 13C are flowcharts each describing a training process in accordance with the second embodiment.
Figure 13B:
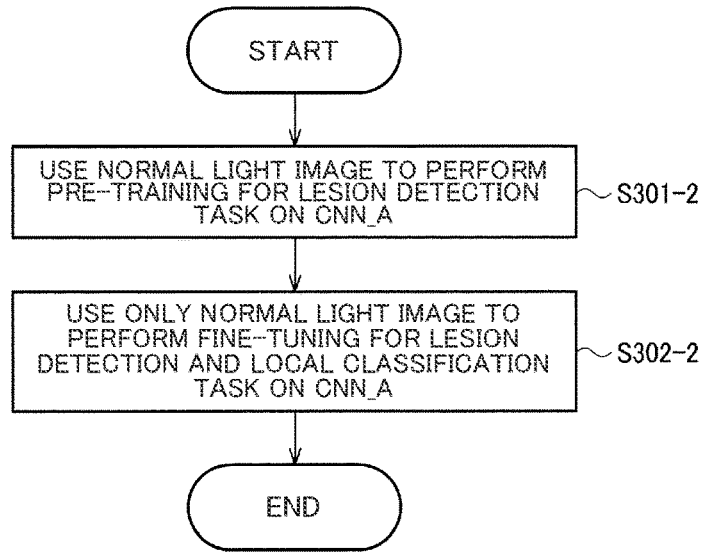
Figure 13C:
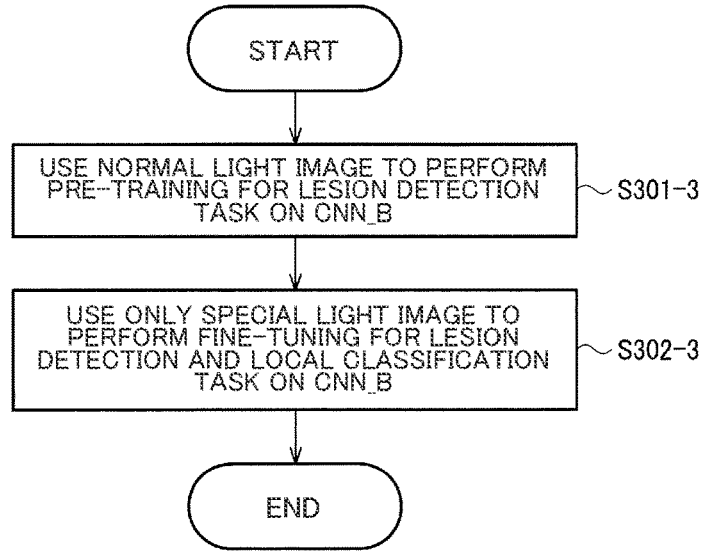

FIGS. 13A to 13C are flowcharts each describing the training process in accordance with the second embodiment. FIG. 13 is a flowchart describing a process of generating the CNN_AB. When this process is started, firstly in step S301-1, the pre-training section 121 uses the normal light image to perform pre-training for a lesion detection task on the CNN_AB. In step S302-1, the observation method-mixed fine-tuning section 123 uses the special light image and the normal light image to perform fine-tuning for a lesion detection and local classification task on the CNN_AB with a pre-training result serving as an initial value.

FIG. 13B is a flowchart describing a process of generating the CNN_A. When this process is started, firstly in step S301-2, the pre-training section 121 uses the normal light image to perform pre-training for the lesion detection task on the CNN_A. In step S302-2, the observation method-specific fine-tuning section 124 uses only the normal light image to perform fine-tuning for the lesion detection and local classification task on the CNN_A with a pre-training result serving as an initial value.

FIG. 13C is a flowchart describing a process of generating the CNN_B. When this process is started, firstly in step S301-3, the pre-training section 121 uses the normal light image to perform pre-training for the lesion detection task on the CNN_B. In step S302-3, the observation method-specific fine-tuning section 124 uses only the special light image to perform fine-tuning for the lesion detection and local classification task on the CNN_B with a pre-training result serving as an initial value.

3.2 Recognition Process

Figure 14:
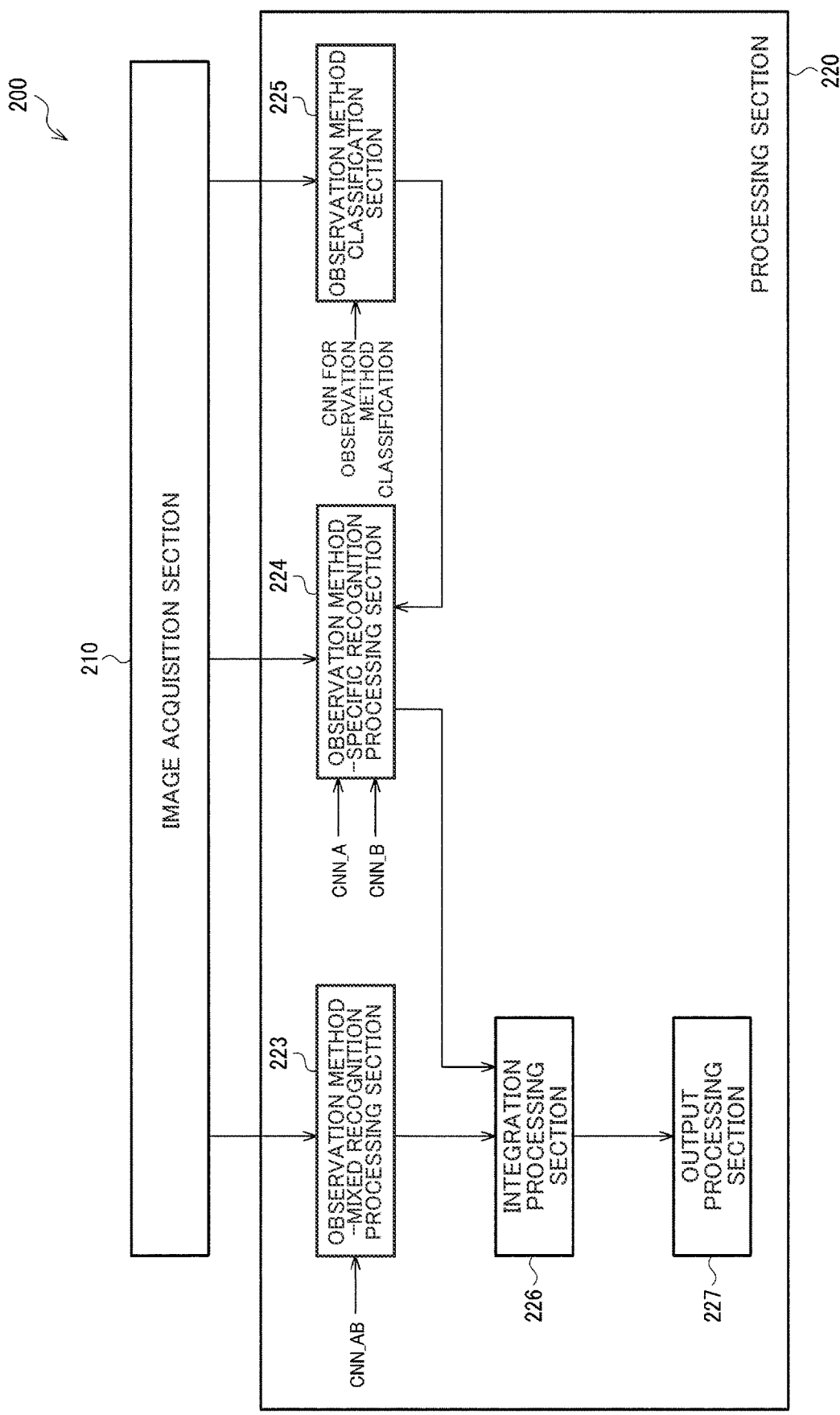
FIG. 14 illustrates a configuration example of an image processing system in accordance with a second embodiment.

FIG. 14 illustrates a configuration example of the image processing system 200 in accordance with the second embodiment. The processing section 220 of the image processing system 200 includes an observation method-mixed recognition processing section 223, an observation method-specific recognition processing section 224, an observation method classification section 225, an integration processing section 226, and an output processing section 227. The observation method-mixed recognition processing section 223 operates in accordance with the trained model generated by the training device 100. The observation method-specific recognition processing section 224 operates in accordance with at least one of the CNN_A or the CNN_B generated by the training device 100. The observation method classification section 225 operates in accordance with the CNN for observation method classification generated by the training device 100. The integration processing section 226 performs an integration process of integrating a recognition result from the observation method-mixed recognition processing section 223 and a recognition result from the observation method-specific recognition processing section 224. The output processing section 227 performs an output process based on a result of the integration process.

Figure 15:
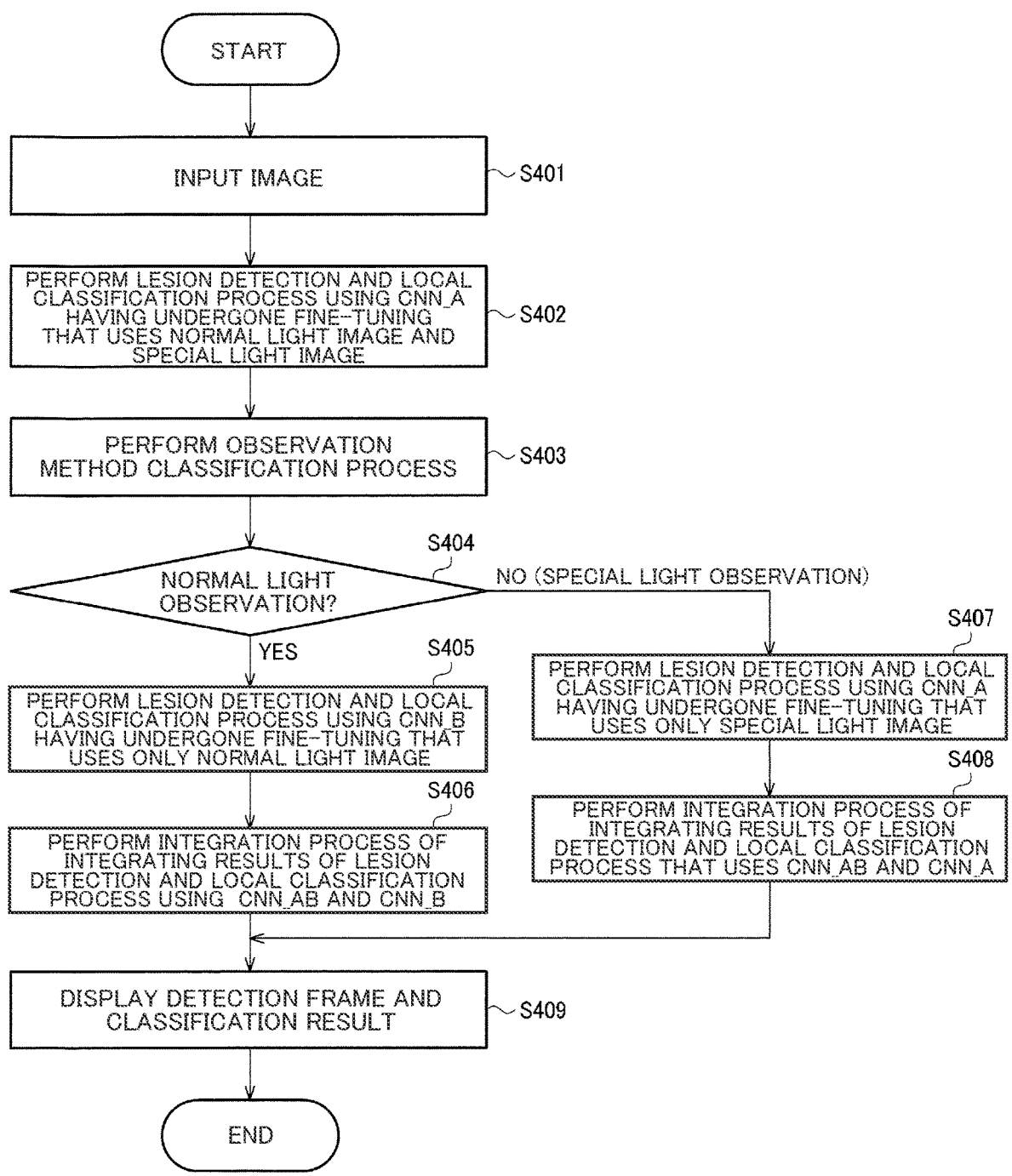
FIG. 15 is a flowchart describing a recognition process in accordance with the second embodiment.

FIG. 15 is a flowchart describing processing of the image processing system 200 in accordance with the second embodiment. Firstly, in step S401, the image acquisition section 210 acquires an in-vivo image captured by the endoscope imaging device as the processing target image.

In steps S402, the observation method-mixed recognition processing section 223 performs calculation in the forward direction with the processing target image acquired by the image acquisition section 210 serving as the input to the CNN_AB. In processing in step S402, the recognition processing section 221 acquires information indicating a detection result from the detection layer and information indicating a local classification result from the local classification layer.

In step S403, the observation method classification section 225 performs an observation method classification process to determine whether the processing target image is the normal light image or the special light image. For example, the observation method classification section 225 inputs the processing target image acquired by the image acquisition section 210 to the CNN for observation method classification, and thereby acquires probability data representing a probability that the processing target image is the normal light image and probability data representing a probability that the processing target image is the special light image. The observation method classification section 225 performs the observation method classification process based on a magnitude relationship between the two pieces of probability data.

Alternatively, the observation method classification section 225 may perform the observation method classification process without using the trained model. For example, the observation method classification section 225 may acquire a signal from a switch for switching between normal light illumination and special light illumination and thereby perform the observation method classification process to classify an illumination state between the normal light illumination and the special light illumination. Alternatively, the observation method classification section 225 may perform the observation method classification process based on color distribution or the like of the processing target image. Since the special light image as the NBI image is, for example, a pseudo-color image, there is a large difference in color distribution between the special light image and the normal light image.

The same applies to a case where the pigment-sprayed image is used instead of the special light image, and the observation method classification section 225 may perform the observation method classification process using the trained model or without using the trained model. In a case where the normal light image and the pigment-sprayed image are classified without using the trained model, a signal from the switch cannot be acquired. For example, the observation method classification section 225 may perform the observation method classification process based on color distribution or the like of the processing target image. For example, in a case where indigocarmine has been sprayed, the pigment-sprayed image has a deeper blue color than that of the normal light image. Alternatively, the user may be made to input whether or not a pigment has been sprayed to perform the observation method classification process.

In step S404, the observation method-specific recognition processing section 224 determines whether the observation method is the normal light observation or the special light observation, based on a result of the observation method classification process. When determining that the observation method is the normal light observation in step S404, in step S405, the observation method-specific recognition processing section 224 performs calculation in the forward direction with the processing target image acquired by the image acquisition section 210 serving as the input to the CNN_A. The observation method-specific recognition processing section 224 performs the processing in step S405 to acquire information indicating a detection result from the detection layer and information indicating a local classification result from the local classification layer.

In step S406, the integration processing section 226 performs an integration process of integrating a recognition result obtained using the CNN_AB and a recognition result obtained using the CNN_A. Even in a case of detection results with respect to the identical region of interest, the position or size of the detection frame output from the CNN_AB and the position or size of the detection frame output from the CNN_A are not necessarily matched with each other. In addition, there is a case where local classification labels associated with the respective detection frames are different from each other. At this time, if both of the recognition result obtained using the CNN_AB and the recognition result obtained using the CNN_A are output, a plurality of pieces of different information with respect to one region of interest are displayed, resulting in confusion for a user.

To address this, the integration processing section 226 determines whether the detection frame detected by the CNN_AB and the detection frame detected by the CNN_A are regions corresponding to the identical region of interest. For example, the integration processing section 226 calculates Intersection over Union (IoU) representing a degree of overlap between the detection frames. In a case where the IoU is a threshold or greater, the integration processing section 226 determines that the two detection frames correspond to the identical region of interest. Since the IoU is a known technique, a detailed description thereof is omitted. The threshold for the IoU is, for example, about 0.5, but a specific numeric value can be modified in various manners.

The integration processing section 226 determines whether or not local classification labels of the two detection frames that are determined to correspond to the identical region of interest are matched with each other. For example, in a case where the NICE classification is used, the integration processing section 226 determines whether or not types having the highest probability data value out of Types 1 to 3 are matched with each other. In a case where the local classification labels are different, the integration processing section 226, for example, performs an integration process to select a local classification label having a higher local classification score and delete a local classification label having a lower local classification score. In a case where the local classification labels are matched with each other, the integration processing section 226 performs a process of selecting one having a higher value out of the local classification score output from the CNN_AB and the local classification score output from the CNN_A, or a process of obtaining an average value of two values thereof, and thereby updates the local classification score.

On the other hand, when determining that the observation method is the special light observation in step S404, in step S407, the observation method-specific recognition processing section 224 performs calculation in the forward direction with the processing target image acquired by the image acquisition section 210 serving as an input to the CNN_B. The observation method-specific recognition processing section 224 performs the processing in step S406 to acquire information indicating a detection result from the detection layer and information indicating a local classification result from the local classification layer.

In step S408, the integration processing section 226 performs an integration process of integrating the recognition result obtained using the CNN_AB and the recognition result obtained using the CNN_B. The flow of the integration process is similar to that in step S406.

As a result of the integration process in step S406 or S408, one recognition result is acquired with respect to one region of interest. That is, the output of the integration process is information indicating detection frames whose number corresponds to the number of regions of interest in the processing target image, the detection score in each detection frame, and the information indicating the local classification label and the local classification score. Hence, the output processing section 227 performs an output process similar to that of the output processing section 222 in the first embodiment. For example, the output processing section 227 performs a process of comparing between the occupied area ratio and the TH1 or a process of comparing between the detection score and the TH2 to select information to be output.

As described above, the processing section 220 in accordance with the present embodiment performs the integration process of integrating a first recognition result obtained by operating in accordance with a first trained model and a second recognition result obtained by operating in accordance with a second trained mode, and outputs a result of the integration process as a recognition result.

The first trained model is, for example, the CNN_AB. The second trained model is, for example, the CNN_A or the CNN_B.

In this manner, integrating a plurality of recognition results enables acquisition of a recognition result with higher accuracy. For example, in a case where data is poorly balanced between the two observation methods, the CNN_A or the CNN_B, which is an observation method-specific trained model, exhibits higher accuracy. In a case where data is well balanced between the two observation methods, the CNN_AB, which is an observation method-mixed trained model, exhibits higher accuracy. The balancing of data represents a ratio of the number of images in an image group used for training.

The balancing of data in the observation method changes due to various factors such as an operational status of the endoscope system serving as a source for collecting data and a status of provision of ground truth. Additionally, in a case where collection is continuously performed, it is assumed that the balancing of data changes with time. While the training device 100 can adjust the balancing of data or change the training process in accordance with the balancing of data, a load of the training process becomes heavier. While the inference process in the image processing system 200 can be changed in consideration of the balancing of data in a training stage, it is necessary to acquire information regarding the balancing of data or to branch processing in accordance with the balancing of data, leading to a heavy load. In this regard, performing the integration process as described above enables presentation of a result with high accuracy in a complementary manner regardless of the balancing of data without increasing a processing load.

In addition, the processing section 220 operates in accordance with the first trained model to obtain, as a detection result, a first region representing a region corresponding to the region of interest, and operates in accordance with the second trained model to obtain, as the detection result, a second region representing a region corresponding to the region of interest, The processing section 220 then determines whether or not the first region and the second region correspond to the identical region of interest based on a degree of overlap between the first region and the second region.

This enables determination of whether or not the two regions output from the respective two trained models are information targeting the identical region of interest. Thus, for example, it is possible to prevent presentation of a plurality of pieces of information that are different with respect to the identical region of interest.

Each of the first region and the second region may be a detection frame surrounding the region of interest in the image. The processing section 220 calculates the IoU representing a degree of overlap between the detection frame corresponding to the first region and the detection frame corresponding to the second region. In a case where the IoU is equal to or greater than a predetermined threshold, the processing section 220 determines that the first region and the second region correspond to the identical region of interest.

This enables determination of whether or not the two detection frames are information targeting the identical region of interest, based on the IoU of the two detection frames. Hence, it is possible to prevent presentation of a plurality of pieces of information that are different with respect to the identical region of interest.

When determining that the first region and the second region are regions corresponding to the identical region of interest in a case where the local classification result corresponding to the first region and the local classification result corresponding to the second region are different from each other, the processing section 220 may perform a process of selecting a local classification result having a higher local classification score representing a probability of the local classification result.

The local classification result mentioned herein represents, specifically, the local classification label. Consequently, even in a case where the local classification results with respect to the identical region of interest are different from each other, it is possible to output the local classification result with a higher probability.

The trained model in accordance with the present embodiment includes a trained model for the second observation method that is trained by having undergone pre-training that uses the first image group and then having undergone fine-tuning that uses the second image group, and a trained model for the first observation method that is trained by having undergone pre-training that uses the first image group and then having undergone fine-tuning that uses a third image group including an image captured in the first observation method.

The first image group mentioned herein corresponds to the C1 in FIG. 12, and is an image group comprising images in each of which the normal light image is provided with the detection data. The second image group corresponds to the C4, and is an image group comprising images in each of which the special light image is provided with the detection data and the local classification data. The third image group corresponds to the C3, and is an image group comprising an image in which the normal light image is provided with the detection data and the local classification data, and an image in which the special light image is provided with the detection data and the local classification data. The trained model for the second observation method corresponds to the CNN_B, and the trained model for the first observation method corresponds to the CNN_A.

This enables usage of the trained model appropriate for an image captured in the first observation method and the trained model appropriate for an image captured in the second observation method for the recognition process. Hence, it is possible to perform the recognition process with high accuracy, regardless of the observation method for the processing target image.

When determining that the processing target image is an image captured in the first observation method, the processing section 220 outputs a recognition result based on the trained model for the first observation method. When determining that the processing target image is an image captured in the second observation method, the processing section 220 outputs a recognition result based on the trained model for the second observation method. For example, the processing section 220 switches, based on a result of the imaging classification process, between operation in accordance with the trained model for the first observation method and operation in accordance with the trained model for the second observation method.

In this manner, selecting an appropriate trained model based on the result of determining the observation method by which the processing target image is captured enables execution of the recognition process with high accuracy. Note that the above description has been given of the example of performing either the recognition process based on the CNN_A or the recognition process based on the CNN_B, but the flow of processing is not limited thereto. For example, the observation method-specific recognition processing section 224 may be configured to perform both the recognition process based on the CNN_A and the recognition process based on the CNN_B, and thereafter output a result of either one of the recognition processes to the integration processing section 226 based on the result of observation method classification.

Additionally, the first image group includes an image in which the image captured in the first observation method is provided with, as the ground truth, the detection data regarding at least one of whether the region of interest is present, and, if any, the position, the size, and the shape of the region of interest, and the third image group includes an image in which the image captured in the first observation method is provided with, as the ground truth, the detection data and the local classification data representing the degree of malignancy of the region of interest.

As described above, it is assumed that as the recognition process in accordance with the present embodiment, the local classification process, in addition to the detection process, is performed. Since the normal light image is used for detecting a lesion in many cases, an abundance of normal light image images provided with the detection data can be acquired. That is, the number of images in the first image group is relatively large. However, since there is no local classification data, it is not possible to generate a trained model for performing the local classification process from the first image group. Since normal light images provided with the local classification data cannot be acquired in abundance, the number of images included in the third image group is relatively small. For this reason, even if full-training is performed using only the third image group, it is not possible to increase accuracy of the recognition process due to insufficiency of the number of images. In this regard, performing pre-training that uses the first image group and fine-tuning that uses the third image group enables generation of the trained model capable of executing the detection process and the local classification process on the normal light image with high accuracy.

4. Third Embodiment

The description has been given of the example in which the second observation method is either the special light observation or the pigment spray observation. However, the observation method is not limited to the case where either the special light observation or the pigment spray observation serves as a processing target, and both the special light observation and the pigment spray observation may serve as the processing target. That is, in a third embodiment, a description will be given of an example in which an observation method includes the normal light observation, the special light observation, and the pigment spray observation.

A configuration of the pre-training section 121 of the training device 100 is similar to that in the first and second embodiments. As image groups to be used for fine-tuning, seven possible image groups comprising an image group A, an image group B, an image group C, an image group AB, and image group BC, an image group CA, and an image group ABC can be assumed. The image group A comprises images in each of which the normal light image is provided with the detection data and the local classification data. The image group B comprises images in each of which the special light image is provided with the detection data and the local classification data. The image group C comprises images in each of which the pigment-sprayed image is provided with the detection data and the local classification data. The image group AB comprises a mixture of the normal light image and the special light image. The image group BC comprises a mixture of the special light image and the pigment-sprayed image. The image group CA comprises a mixture of the pigment-sprayed image and the normal light image. The image group ABC comprises a mixture of the normal light image, the special light image, and the pigment-sprayed image.

For example, the observation method-mixed fine-tuning section 123 performs fine-tuning that generates CNN_ABC based on the image group ABC, fine-tuning that generates CNN_AB based on the image group AB, fine-tuning that generates CNN_BC based on the image group BC, and fine-tuning that generates CNN_CA based on the image group CA. The observation method-specific fine-tuning section 124 performs fine-tuning that generates CNN_A based on the image group A, fine-tuning that generates CNN_B based on the image group B, and fine-tuning that generates CNN_C based on the image group C.

The observation method classification section 225 performs the observation method classification process to determine which of the normal light observation, the special light observation, and the pigment spray observation is performed in the observation method by which the processing target image is captured. The observation method classification process may be performed using the trained model similarly to the second embodiment, or may be performed using color distribution of the processing target image.

In a case where a result of the observation method classification process is the normal light observation, the observation method-mixed recognition processing section 223 uses the CNN_AB, the CNN_CA, and the CNN_ABC to acquire three recognition results. The observation method-specific recognition processing section 224 uses the CNN_A to acquire one recognition result. The integration processing section 226 performs an integration process of integrating the acquired four recognition results. Although the number of integration targets increases to four, the flow of the specific integration process is similar to that in the second embodiment. That is, the integration processing section 226 determines whether or not a plurality of detection frames correspond to the identical region of interest based on a degree of overlap between the detection frames. When determining that the plurality of detection frames corresponds to the identical region of interest, the integration processing section 226 compares the local classification labels of the respective detection frames. In a case where the local classification labels are different, the integration processing section 226, for example, performs a process of selecting a local classification label having the highest local classification score. In a case where the local classification labels are matched with each other, the integration processing section 226 uses the highest value of the local classification scores or an average value of the local classification scores to update the local classification score.

In a case where a result of the observation method classification process is the special light observation, the observation method-mixed recognition processing section 223 uses the CNN_AB, the CNN_BC, and the CNN_ABC to acquire three recognition results. The observation method-specific recognition processing section 224 uses the CNN_B to acquire one recognition result. The integration processing section 226 performs an integration process of integrating the acquired four recognition results.

In a case where a result of the observation method classification process is the pigment spray observation, the observation method-mixed recognition processing section 223 uses the CNN_BC, the CNN_CA, and the CNN_ABC to acquire three recognition results. The observation method-specific recognition processing section 224 uses the CNN_C to acquire one recognition result. The integration processing section 226 performs an integration process of integrating the acquired four recognition results.

As described above, the method in accordance with the present disclosure can be extended also to a case of using three or more observation methods. In this manner, integrating the plurality of recognition results enables presentation of the recognition result with higher accuracy.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

What is claimed is:

1. An image processing system comprising:
a processor including hardware, the processor being configured to:
  acquire, as a processing target image, an in-vivo image captured by an endoscope imaging device,
  operate in accordance with a trained model, and
  output a recognition result representing a result of recognition of a region of interest in the processing target image,
the trained model being trained by having undergone pre-training that uses a first image group including images captured in a first observation method, and then having undergone, after the pre-training, fine-tuning that uses a second image group including images captured in a second observation method, as well as that uses ground truth regarding the region of interest included in the second image group,
the first observation method being an observation method that uses normal light as illumination light,
the second observation method being an observation method that uses special light as the illumination light or an observation method in which a pigment has been sprayed onto a subject,
the second image group including at least one image captured with the region of interest,
the second image group being lesser in number of images than the first image group;
the ground truth being data including at least one of:
  detection data regarding at least one of whether the region of interest is present in an image, and, if any, a position, a size, and a shape of the region of interest, and
  local classification data regarding a degree of malignancy of the region of interest in the image, and
the recognition result being a result including at least one of:
  a detection result regarding at least one of whether the region of interest is present in the image, and, if any, the position, the size, and the shape of the region of interest, and
  a local classification result regarding the degree of malignancy of the region of interest in the image.

2. The image processing system as defined in claim 1, wherein the region of interest is a polyp.

3. The image processing system as defined in claim 1,
wherein the processor obtains, based on the trained model, a detection score representing a probability of the detection result and a local classification score representing a probability of the local classification result, and
wherein the processor outputs, in a case where the detection score is greater than a given detection threshold, the detection score, and outputs, in a case where the local classification score is greater than a given classification threshold, the local classification result.

4. The image processing system as defined in claim 1,
wherein the processor determines, based on the detection result, whether or not a condition regarding at least one of the size of the region of interest, blur, or motion blur is satisfied,
wherein the processor outputs, in a case where the condition is satisfied, the detection result and the local classification result, and
wherein the processor outputs, in a case where the condition is not satisfied, the detection result without outputting the local classification result.

5. The image processing system as defined in claim 1, wherein the processor performs an integration process of integrating a first recognition result obtained by operating in accordance with a first trained model and a second recognition result obtained by operating in accordance with a second trained model, and outputs a result of the integration process as the recognition result.

6. The image processing system as defined in claim 1,
wherein the processor operates in accordance with a first trained model to obtain, as the detection result, a first region representing a region corresponding to the region of interest, and operates in accordance with a second trained model to obtain, as the detection result, a second region representing a region corresponding to the region of interest, and
wherein the processor determines, based on a degree of overlap between the first region and the second region, whether or not the first region and the second region correspond to an identical region of interest.

7. The image processing system as defined in claim 6,
wherein each of the first region and the second region is a detection frame surrounding the region of interest in the image, and
wherein the processor calculates an Intersection over Union (IoU) representing the degree of overlap between the detection frame corresponding to the first region and the detection frame corresponding to the second region, and determines, in a case where the IoU is equal to or greater than a predetermined threshold, that the first region and the second region correspond to the identical region of interest.

8. The image processing system as defined in claim 6, wherein the processor performs, when determining that the first region and the second region correspond to the identical region of interest in a case where the local classification result corresponding to the first region and the local classification result corresponding to the second region are different from each other, a process of selecting the local classification result having a higher score as a local classification score representing a probability of the local classification result.

9. The image processing system as defined in claim 1, wherein the trained model comprises a convolutional neural network (CNN).

10. The image processing system as defined in claim 1, wherein the trained model includes
a trained model for the second observation method that is trained by having undergone pre-training that uses the first image group, and then having undergone fine-tuning that uses the second image group, and
a trained model for the first observation method that is trained by having undergone pre-training that uses the first image group, and then having undergone fine-tuning that uses a third image group including images captured in the first observation method.

11. The image processing system as defined in claim 10,
wherein the first image group includes an image in which each image captured in the first observation method is provided with, as the ground truth, the detection data regarding at least one of whether the region of interest is present, and, if any, the position, the size, and the shape of the region of interest, and
wherein the third image group includes an image in which each image captured in the first observation method is provided with, as the ground truth, the detection data and local classification data representing the degree of malignancy of the region of interest.

12. The image processing system as defined in claim 1,
wherein the trained model includes a feature amount extraction layer that outputs a feature amount based on the processing target image, a detection layer that outputs information indicating the detection result based on the feature amount, and a local classification layer that outputs the local classification result based on the feature amount,
wherein the trained model is trained in a weight coefficient of the feature amount extraction layer and a weight coefficient of the detection layer by having undergone the pre-training that uses the first image group including images provided with the detection data as the ground truth, and
wherein the trained model is trained in the weight coefficient of the feature amount extraction layer, the weight coefficient of the detection layer, and a weight coefficient of the local classification layer by having undergone the fine-tuning that uses the second image group including images provided with the detection data and the local classification data as the ground truth.

13. A training device comprising:
a processor including hardware, the processor being configured to:
acquire, a first image group including images captured in a first observation method and a second image group including images captured in a second observation method,
generate a trained model that outputs, when a processing target image is input to the trained model, a recognition result representing a result of recognition of a region of interest in the processing target image by having undergone pre-training that uses the first image group, and then having undergone, after the pre-training, fine-tuning that uses the second image group, as well as that uses ground truth regarding the region of interest included in the second image group,
the first observation method being an observation method that uses normal light as illumination light,
the second observation method being an observation method that uses special light as the illumination light or an observation method in which a pigment has been sprayed onto a subject, the second image group including at least one image captured with the region of interest, the second image group being lesser in number of images than the first image group;

the ground truth being data including at least one of:
 detection data regarding at least one of whether the region of interest is present in an image, and, if any, a position, a size, and a shape of the region of interest, and
 local classification data regarding a degree of malignancy of the region of interest in the image, and the recognition result being a result including at least one of:
 a detection result regarding at least one of whether the region of interest is present in the image, and, if any, the position, the size, and the shape of the region of interest, and
 a local classification result regarding the degree of malignancy of the region of interest in the image.

14. A training method comprising:

acquiring a first image group including images captured in a first observation method and a second image group including images captured in a second observation method;

generating a trained model that outputs, when a processing target image is input to the trained model, a recognition result representing a result of recognition of a region of interest in the processing target image by having undergone pre-training that uses the first image group, and then having undergone, after the pre-training, fine-tuning that uses the second image group, as well as that uses ground truth regarding the region of interest included in the second image group, the first observation method being an observation method that uses normal light as illumination light, the second observation method being an observation method that uses special light as the illumination light or an observation method in which a pigment has been sprayed onto a subject, the second image group including at least one image captured with the region of interest, the second image group being lesser in number of images than the first image group;

the ground truth being data including at least one of:
 detection data regarding at least one of whether the region of interest is present in an image, and, if any, a position, a size, and a shape of the region of interest, and
 local classification data regarding a degree of malignancy of the region of interest in the image, and the recognition result being a result including at least one of:
 a detection result regarding at least one of whether the region of interest is present in the image, and, if any, the position, the size, and the shape of the region of interest, and
 a local classification result regarding the degree of malignancy of the region of interest in the image.

15. A computer readable non-transitory storage medium that stores a program that causes a computer to execute steps of:

acquiring, as a processing target image, an in-vivo image captured by an endoscope imaging device;

operating in accordance with a trained model; and outputting a recognition result representing a result of recognition of a region of interest in the processing target image, the trained model being trained by having undergone pre-training that uses a first image group including images captured in a first observation method, and then having undergone, after the pre-training, fine-tuning that uses a second image group including images captured in a second observation method, as well as that uses ground truth regarding the region of interest included in the second image group, the first observation method being an observation method that uses normal light as illumination light, the second observation method being an observation method that uses special light as the illumination light or an observation method in which a pigment has been sprayed onto a subject, the second image group including at least one image captured with the region of interest, the second image group being lesser in number of images than the first image group;

the ground truth being data including at least one of:
 detection data regarding at least one of whether the region of interest is present in an image, and, if any, a position, a size, and a shape of the region of interest, and
 local classification data regarding a degree of malignancy of the region of interest in the image, and the recognition result being a result including at least one of:
 a detection result regarding at least one of whether the region of interest is present in the image, and, if any, the position, the size, and the shape of the region of interest, and
 a local classification result regarding the degree of malignancy of the region of interest in the image.

\* \* \* \* \*